(12) United States Patent
Hildebrandt et al.

(10) Patent No.: US 11,063,222 B2
(45) Date of Patent: Jul. 13, 2021

(54) ORGANIC SEMICONDUCTING MATERIAL AND USE THEREOF IN ORGANIC DEVICES

(71) Applicant: Heliatek GmbH, Dresden (DE)

(72) Inventors: Dirk Hildebrandt, Ulm (DE); Olga Gerdes, Ulm (DE); Roland Fitzner, Ulm (DE); Daniel D'Souza, Dresden (DE); Gunter Mattersteig, Ulm (DE); Andre Weiss, Dresden (DE)

(73) Assignee: HELIATEK GMBH, Dresden (DE)

( * ) Notice: Subject to any disclaimer, the term of this patent is extended or adjusted under 35 U.S.C. 154(b) by 0 days.

(21) Appl. No.: 16/067,631

(22) PCT Filed: Dec. 30, 2016

(86) PCT No.: PCT/EP2016/082901
§ 371 (c)(1),
(2) Date: Jul. 2, 2018

(87) PCT Pub. No.: WO2017/114938
PCT Pub. Date: Jul. 6, 2017

(65) Prior Publication Data
US 2019/0006599 A1    Jan. 3, 2019

(30) Foreign Application Priority Data

Dec. 30, 2015 (DE) .................. 10 2015 123 006.2
Jul. 26, 2016 (EP) .................... 16181347

(51) Int. Cl.
*H01L 51/00* (2006.01)
*C07D 405/14* (2006.01)
(Continued)

(52) U.S. Cl.
CPC ........ *H01L 51/0067* (2013.01); *C07D 405/14* (2013.01); *C07D 409/14* (2013.01);
(Continued)

(58) Field of Classification Search
CPC ............. H01L 51/0067; H01L 51/0068; H01L 51/0065; H01L 51/441; H01L 51/4253;
(Continued)

(56) References Cited

U.S. PATENT DOCUMENTS

2007/0090371 A1    4/2007  Drechsel et al.
2013/0160829 A1    6/2013  Uhrich et al.
(Continued)

FOREIGN PATENT DOCUMENTS

DE    102004014046 A1    9/2004
EP    2483267 B1    8/2013
(Continued)

OTHER PUBLICATIONS

Oruga et al, Greenish metal-lustrous organic crystals formed from 1-aryl-2-(2-thienyl)-5-(5-tricyanoethenyl-2-furyl)pyrroles (Year: 2005).*
(Continued)

*Primary Examiner* — Uyen M Tran
(74) *Attorney, Agent, or Firm* — Leydig, Voit & Mayer, Ltd.

(57) ABSTRACT

A compound of a formula EWG1-(T1)$_a$-(T2)$_b$-(Z)$_c$-(T3)$_d$-(T4)$_e$-EWG2 capable of use as a functional component in organic electronic devices, which enable improved absorption in organic solar cells or have an increased charge carrier mobility.

33 Claims, 5 Drawing Sheets

(51) Int. Cl.
| | |
|---|---|
| *C07D 409/14* | (2006.01) |
| *H01L 51/42* | (2006.01) |
| *C07D 413/12* | (2006.01) |
| *H01L 51/44* | (2006.01) |

(52) U.S. Cl.
CPC ...... *H01L 51/0065* (2013.01); *H01L 51/0068* (2013.01); *C07D 413/12* (2013.01); *H01L 51/4253* (2013.01); *H01L 51/441* (2013.01); *Y02E 10/549* (2013.01)

(58) Field of Classification Search
CPC .. C07D 409/14; C07D 413/12; C07D 405/14; Y02E 10/549
See application file for complete search history.

(56) References Cited

U.S. PATENT DOCUMENTS

| | | | |
|---|---|---|---|
| 2013/0167930 | A1 | 7/2013 | Hildebrandt et al. |
| 2013/0240027 | A1* | 9/2013 | Zakhidov .............. H01L 51/444 136/255 |

FOREIGN PATENT DOCUMENTS

| | | |
|---|---|---|
| WO | WO 2011161108 A1 | 12/2011 |
| WO | WO 2015044377 A1 | 4/2015 |

OTHER PUBLICATIONS

Sunil Kumar, et al., "Effect of N-α Substitution on the Electropolymerization of N-Subsitituted Pyrroles: Structure-Reactivity Relationship Studies", J. Phys. Chem. C 2014, vol. 118, Dec. 2014, pp. 2570-2579.
Gour Hari Jana, et al., Synthesis of some diguanidino 1-methyl-2,5-diary)-1 H-pyrroles as antifungal agents, Bioorganic & Medicinal Chemistry Letters 15 (2005), Dec. 2005, pp. 3592-3595.
Roland Fitzner, "Dicyanovinyl-Substituted Oligothiophenes: Structure-Property Relationships and Application in Vacuum-Processed Small-Molecule Organic Solar Cells", Adv. Funct. Mater., vol. 21, Dec. 2011, pp. 897-910.
I.I. Popov, et al., "Synthesis of β-(4, 5-Dihalofuryl) Acrylic and—Propiolic Acids", Chem. Heterocycl. Compd., vol. 14, No. 3, Dec. 1978, pp. 253-255.
Ting Qi, et al., "Synthesis and properties of fluorine or carbazole-based and dicyanovinyl-capped n-type organic semiconductors", J. Mater. Chem., 2008, vol. 18, Dec. 2008, pp. 1131-1138.
Michael Smith, "Chapter 12: Aliphatic, Alkenyl, and Alkynyl Substitution, Electrophilic and Organometalic", March's Advanced Organic Chemistry: Reactions, Mechanisms, and Structure, Seventh Edition, May 2013, pp. 649-731.
Michael Smith, "Chapter 13: Aromatic Substitution: Nucleophilic and Organometallic", March's Advanced Organic Chemistry: Reactions, Mechanisms, and Structure, Seventh Edition, May 2013, pp. 732-802.
Michael Smith, "Chapter 16: Addition to Carbon.Hetero Multiple Bonds", March's Advanced Organic Chemistry: Reactions, Mechanisms, and Structure, Seventh Edition, May 2013, pp. 1067-1252.
Michael Smith, "Chapter 17: Eliminations", March's Advanced Organic Chemistry: Reactions, Mechanisms, and Structure, Seventh Edition, May 2013, pp. 1253-1320.
Michael Smith, "Chapter 19: Oxidations and Reductions", March's Advanced Organic Chemistry: Reactions, Mechanisms, and Structure, Seventh Edition, May 2013, pp. 1433-1567.
Norio Miyaura, "Metal-Catalyzed Cross-Coupling Reactions of Organoboron Compounds with Organic Halides", Metal-Catalyzed Cross-Coupling Reactions, 2nd Edition, Jan. 30, 2008, pp. 41-123.
Terence N. Mitchell, "Organotin Reagents in Cross-Coupling Reactions", Metal-Catalyzed Cross-Coupling Reactions, 2nd Edition, Jan. 30, 2008, pp. 125-161.
Scott E. Denmark, et al., "Organosilicon Compounds in Cross-Coupling Reactions", Metal-Catalyzed Cross-Coupling Reactions, 2nd Edition, Jan. 30, 2008, pp. 163-216.
Paul Knochel, et al., "Carbon-Carbon Bond-Forming Reactions Mediated by Organozinc Reagents", Metal-Catalyzed Cross-Coupling Reactions, 2nd Edition, Jan. 30, 2008, pp. 619-670.
Paul Knochel, et al., "Carbon-Carbon Bond-Forming Reactions Mediated by Organomagnesium Reagents", Metal-Catalyzed Cross-Coupling Reactions, 2nd Edition, Jan. 30, 2008, pp. 671-698.
Ei-Ichi Negishi, et al., "Palladium- or Nickel-Catalyzed Cross-Coupling with Organometals Containing Zinc, Aluminum, and Zirconium: The Negishi Coupling", Metal-Catalyzed Cross-Coupling Reactions, 2nd Edition, Jan. 30, 2008, pp. 815-889.
L. Groenendaal, et al., "Synthesis of α-monobrominated Pyrrole Derivatives", Synthetic Communications, vol. 25, No. 10, Dec. 1995, pp. 1589-1600.
Ogura K et al: "Greenish metal-lustrous organic crystals formed from 1-aryl-2-(2-thienyl)-5-(5-tricyanoethenyl-2-furyl)pyrroles", Tetrahedron, Elsevier Science Publishers, Amsterdam, NL, vol. 62, No. 10, Mar. 6, 2006 (Mar. 6, 2006), pp. 2413-2419, XP025001640.
Hai Fu et al: "Palladium-Catalysed Direct Heteroarylations of Heteroaromatics Using Esters as Blocking Groups at C2 of Bromofuran and Bromothiophene Derivatives: A One-Step Access to Biheteroaryls", SYNLETT, vol. 23, No. 14, Aug. 8, 2012 (Aug. 8, 2012), pp. 2077-2082, XP055358643.
Martin Pfeiffer, "Controlled Doping of Organic Vacuum Deposited Dy Layers: Basics and Applications", Dec. 1999, pp. 1-155.

* cited by examiner

ORGANIC SEMICONDUCTING MATERIAL AND USE THEREOF IN ORGANIC DEVICES

CROSS-REFERENCE TO PRIOR APPLICATIONS

This application is a U.S. National Stage Application under 35 U.S.C. § 371 of International Application No. PCT/EP2016/082901 filed on Dec. 30, 2016 and claims benefit to German Patent Application No. DE 10 2015 123 006.2, filed on Dec. 30, 2015, and European Patent Application No. EP 16181347.2, filed on Jul. 26, 2016. The International Application was published in German on Jul. 6, 2017, as WO 2017/114938 A1 under PCT Article 21(2).

FIELD

The invention relates to an organic semiconducting materials and to the use thereof in semiconducting components.

BACKGROUND

Organic electronics use interconnections of electrically conductive polymers or small organic molecules. Organic-electronic components in this context may be, for example, displays, data memories or transistors, including field-effect transistors in particular. These components also comprise organic-optoelectronic components, examples being organic photoactive components such as solar cells and photodetectors, which comprise a photoactive layer in which incident radiation generates charge carriers, e.g., bound electron-hole pairs (excitons). Further optoelectronic components are light-emitting electroluminescent components, which emit light when a current flows through them. Optoelectronic components comprise at least two electrodes, with one electrode being applied on a substrate and the other acting as a counterelectrode. Located between the electrodes is at least one photoactive layer, preferably an organic photoactive layer. Further layers, transport layers for example, may be disposed between the electrodes.

Through the use of suitable innovative organic materials it is possible to provide a variety of innovative components. There is therefore an interest in development of new applications which are thin, flexible, lightweight, and also have color variability and in addition are inexpensive.

SUMMARY

An embodiment of the present invention provides compounds of the general formula I:

EWG1-(T1)$_a$-(T2)$_b$-(Z)$_c$-(T3)$_d$-(T4)$_e$-EWG2 with the parameters a, b, d and e being each independently of one another 0 or 1, with the parameter c being 1, 2, 3, 4 or 5, where the general group Z is a block of two groups M and N, linked as *-M-N—* or *—N-M-*, where * designates the attachment to the groups T1 to T4 or EWG1 or EWG2, where the groups M each independently of one another are selected from:

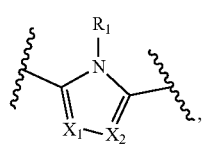

Formula 1

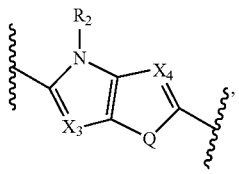

Formula 2

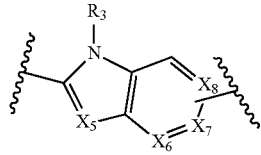

Formula 3 where the groups N each independently of one another are selected from:

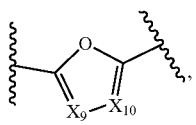

Formula 4

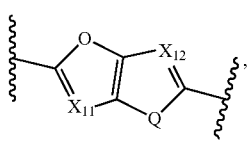

Formula 5

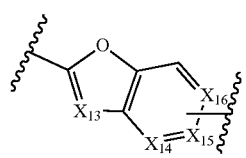

Formula 6 where M and N are each linked such that at least one N atom of the group M and one O atom of the group N are each joined to one another via 2 C atoms, and $l$ designates the attachment to the other groups in the compound of the general formula I, with $X_1$-$X_{16}$ independently of one another being selected from N or C—R, with the proviso that in the groups of the formulae 3 and 6, in each case one group from the groups $X_8$/$X_7$ and $X_{16}$/$X_{15}$ designates the attachment $l$ to the other groups in the compound of the general formula I, with each R independently of any other being selected from a group composed of H, halogen, branched or linear, cyclic or open-chain $C_1$-$C_{20}$ alkyl, where hydrogen atoms of the $C_1$-$C_{20}$ alkyl may be substituted, where the substituent may in particular be halogen, e.g., F, and C atoms of the $C_1$-$C_{20}$ alkyl may be replaced by heteroatoms, such as O or S; $C_2$-$C_{20}$ alkenyl, O-alkyl, S-alkyl, O-alkenyl, S-alkenyl, alkynyl, aryl, heteroaryl, it being possible for hydrogen atoms to be substituted in all of these groups (substituted O-alkyl groups preferred); CN, NR'R", with R' and R" each independently of one another being selected from: H, branched or linear, cyclic or open-chain $C_1$-$C_{20}$ alkyl, where hydrogen atoms of the $C_1$-$C_{20}$ alkyl may be substituted, e.g., by halogen, and C atoms of the $C_1$-$C_{20}$ alkyl may be replaced by heteroatoms, e.g., O or S, where $R_1$, $R_2$, $R_3$ each independently of one another are selected from a group composed of H, branched or linear, cyclic or open-chain $C_1$-$C_{20}$ alkyl, where hydrogen atoms of the $C_1$-$C_{20}$ alkyl may be substituted, preferably by halogen, and C atoms of the $C_1$-$C_{20}$ alkyl may be replaced by heteroatoms, e.g., O or S; substituted or unsubstituted $C_2$-$C_{20}$ alkenyl, substituted or unsubstituted aryl, substituted or unsubstituted heteroaryl, CN, with each Q independently of any other being selected from S, O, Se, NR''', where R''' is defined as for $R_1$ to $R_3$, where the electron-withdrawing groups EWG1 and EWG2 independently of one another are electron-withdrawing groups having at least one C=C double bond, where the groups T1, T2, T3 and T4 each independently of one another are selected from:

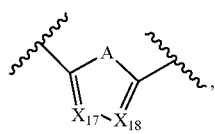

Formula 10

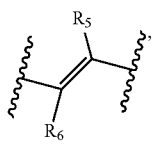

Formula 11

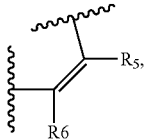

Formula 11*

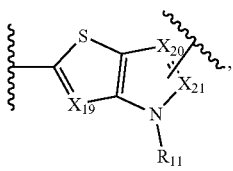

Formula 12

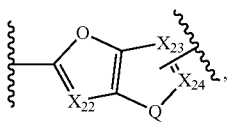

Formula 13

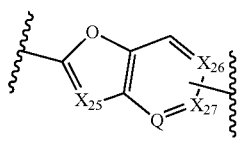

Formula 14

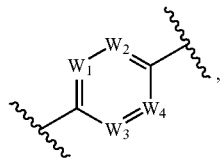

Formula 15

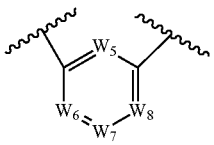

Formula 16 and $\ell$ designates the attachment to the other groups in the compound of the general formula I, with $R_5$ and $R_6$ each independently of one another being selected from a group: H, CN, F, aryl, heteroaryl, $C_2$-$C_{20}$ alkenyl, $C_2$-$C_{20}$ alkynyl, branched or linear, cyclic or open-chain $C_1$-$C_{20}$ alkyl, where hydrogen atoms of the $C_1$-$C_{20}$ alkyl may be substituted, e.g., by halogen, where, if the substituent $R_{13}$ is present in the compound of the formula I, a ring closure between $R_5$ with $R_{13}$ or $R_6$ with $R_{13}$ is possible, with the proviso that between $R_5$ and $R_{13}$ or between $R_6$ and $R_{13}$ in each case the double bond from formula 11 or 11* is located, is possible, with $W_1$ to $W_8$ each independently of one another being selected from N, CR, where R is defined as described above, with $X_{17}$ to $X_{27}$ independently of one another being selected from C—R, where R is defined as described above, and with the proviso that in the groups of the formulae 12, 13 and 14, in each case one group from the groups $X_{20}/X_{21}$, $X_{23}/X_{24}$ and $X_{26}/X_{27}$ designates the attachment $\ell$ to the other groups in the compound of the general formula I, with A being S, O, NR'''', Se with Q being S, O, NR'''', Se where for the groups A and Q, the substituent R'''' in each case independently of any other is selected from H, CN, branched or linear, cyclic or open-chain $C_1$-$C_{20}$ alkyl, where the H atoms of the $C_1$-$C_{20}$ alkyl may be substituted, where there may in particular be substitution by halogen, e.g., F; $C_2$-$C_{20}$ alkenyl, O-alkyl, S-alkyl, O-alkenyl, S-alkenyl, alkynyl, substituted or unsubstituted aryl, substituted or unsubstituted heteroaryl.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1:
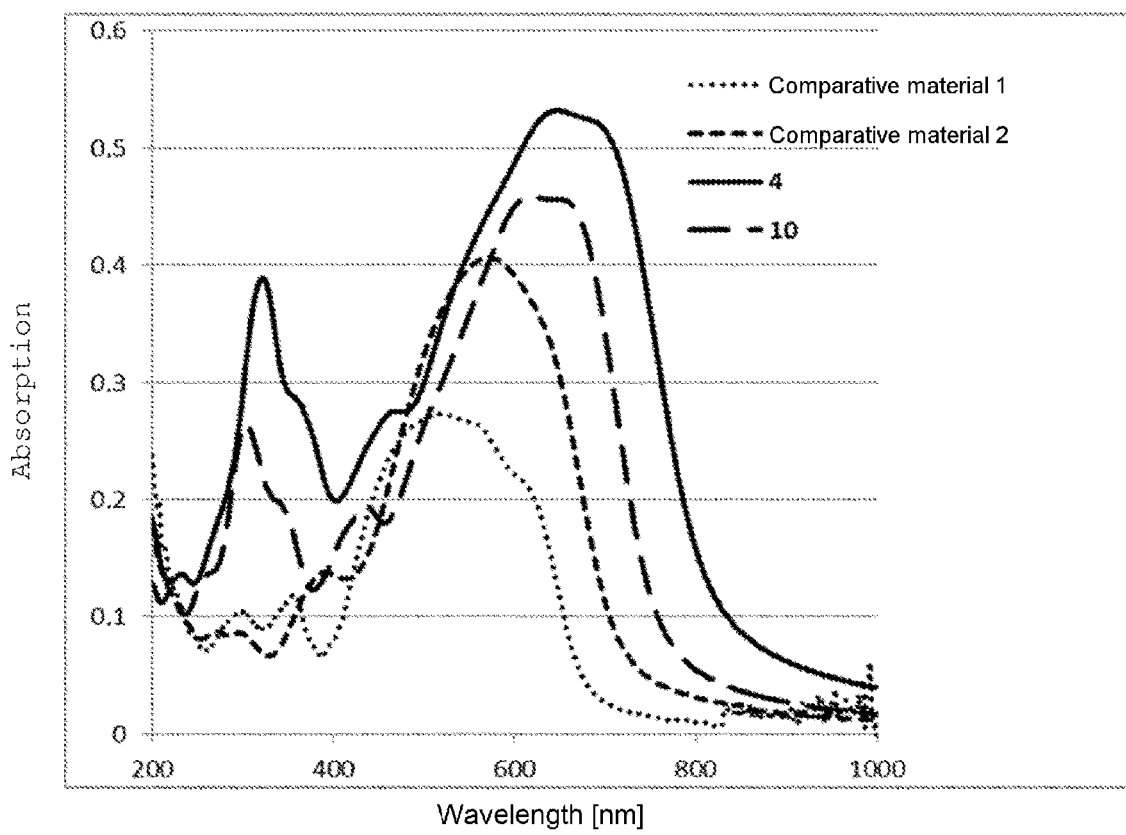
FIGS. 1 to 3 show the absorption spectra of compounds of the present invention in comparison to unclaimed compounds.

There continues to be a search for organic semiconducting materials to use in organic electronic components that result in an improvement in the properties of the components.

Embodiments of the present invention are directed to compounds of the general formula I (see below) that result in an improvement of properties of organic electronic components. Further advantageous embodiments of the compounds, and also advantageous uses of the compounds of the invention, and organic electronic components comprising these compounds, are described below.

Embodiments of the present invention include compounds of the general formula I:

$$\text{EWG1-(T1)}_a\text{-(T2)}_b\text{-(Z)}_c\text{-(T3)}_d\text{-(T4)}_e\text{-EWG2}$$

with the parameters a, b, d and e being each independently of one another 0 or 1,
with the parameter c being 1, 2, 3, 4 or 5,
where the general group Z is a block of two groups M and N, linked as *-M-N—* or *—N-M-*, where * designates the attachment to the groups T1 to T4 or EWG1 or EWG2,
where the groups M each independently of one another are selected from:

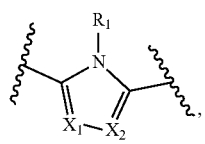

Formula 1

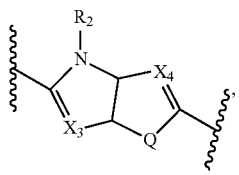

Formula 2

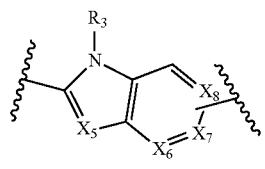

Formula 3 where the groups N each independently of one another are selected from:

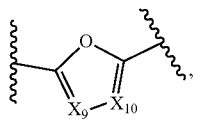

Formula 4

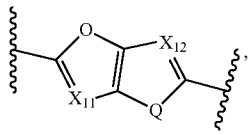

Formula 5

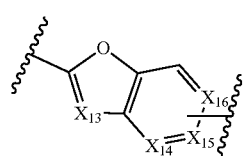

Formula 6 where M and N are each linked such that at least one N atom of the group M and one O atom of the group N are each joined to one another via 2 C atoms, and ∫ designates the attachment to the other groups in the compound of the general formula I, with $X_1$-$X_{16}$ independently of one another being selected from N or C—R, with the proviso that in the groups of the formulae 3 and 6, in each case one group from the groups $X_8$/$X_7$ and $X_{16}$/$X_{15}$ designates the attachment ∫ to the other groups in the compound of the general formula I, with each R independently of any other being selected from a group composed of H, halogen, branched or linear, cyclic or open-chain $C_1$-$C_{20}$ alkyl, where hydrogen atoms of the $C_1$-$C_{20}$ alkyl may be substituted, where the substituent may in particular be halogen, e.g., F, and C atoms of the $C_1$-$C_{20}$ alkyl may be replaced by heteroatoms, such as O or S; $C_2$-$C_{20}$ alkenyl, O-alkyl, S-alkyl, O-alkenyl, S-alkenyl, alkynyl, aryl, heteroaryl, it being possible for hydrogen atoms to be substituted in all of these groups (substituted O-alkyl groups preferred); CN, NR'R", with R' and R" each independently of one another being selected from: H, branched or linear, cyclic or open-chain $C_1$-$C_{20}$ alkyl, where hydrogen atoms of the $C_1$-$C_{20}$ alkyl may be substituted, e.g., by halogen, and C atoms of the $C_1$-$C_{20}$ alkyl may be replaced by heteroatoms, e.g., O or S, where $R_1$, $R_2$, $R_3$ each independently of one another are selected from a group composed of H, branched or linear, cyclic or open-chain $C_1$-$C_{20}$ alkyl, where hydrogen atoms of the $C_1$-$C_{20}$ alkyl may be substituted, preferably by halogen, and C atoms of the $C_1$-$C_{20}$ alkyl may be replaced by heteroatoms, e.g., O or S; substituted or unsubstituted $C_2$-$C_{20}$ alkenyl, substituted or unsubstituted aryl, substituted or unsubstituted heteroaryl, CN, with each Q independently of any other being selected from S, O, Se, NR''', where R''' is defined as for $R_1$ to $R_3$, where the electron-withdrawing groups EWG1 and EWG2 independently of one another are electron-withdrawing groups having at least one C=C double bond, where the groups T1, T2, T3 and T4 each independently of one another are selected from:

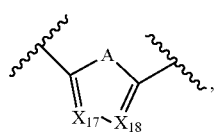

Formula 10

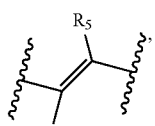

Formula 11

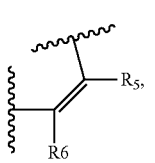

Formula 11*

-continued

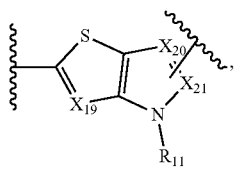
Formula 12

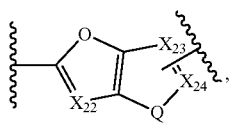
Formula 13

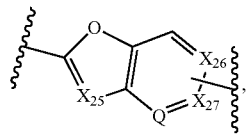
Formula 14

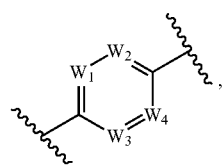
Formula 15

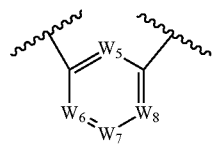
Formula 16 and ⌇ designates the attachment to the other groups in the compound of the general formula I, with $R_5$ and $R_6$ each independently of one another being selected from a group: H, CN, F, aryl, heteroaryl, $C_2$-$C_{20}$ alkenyl, $C_2$-$C_{20}$ alkynyl, branched or linear, cyclic or open-chain $C_1$-$C_{20}$ alkyl, where hydrogen atoms of the $C_1$-$C_{20}$ alkyl may be substituted, e.g., by halogen, where, if the substituent $R_{13}$ is present in the compound of the formula I, a ring closure between $R_5$ with $R_{13}$ or $R_6$ with $R_{13}$ is possible, with the proviso that between $R_5$ and $R_{13}$ or between $R_6$ and $R_{13}$ in each case the double bond from formula 11 or 11* is located, is possible, with $W_1$ to $W_8$ each independently of one another being selected from N, CR, where R is defined as described above, with $X_{17}$ to $X_{27}$ independently of one another being selected from C—R, where R is defined as described above, and with the proviso that in the groups of the formulae 12, 13 and 14, in each case one group from the groups $X_{20}/X_{21}$, $X_{23}/X_{24}$ and $X_{26}/X_{27}$ designates the attachment ⌇ to the other groups in the compound of the general formula I, with A being S, O, NR'''', Se
with Q being S, O, NR'''', Se
where for the groups A and Q, the substituent R'''' in each case independently of any other is selected from H, CN, branched or linear, cyclic or open-chain $C_1$-$C_{20}$ alkyl, where the H atoms of the $C_1$-$C_{20}$ alkyl may be substituted, where there may in particular be substitution by halogen, e.g., F; $C_2$-$C_{20}$ alkenyl, O-alkyl, S-alkyl, O-alkenyl, S-alkenyl, alkynyl, substituted or unsubstituted aryl, substituted or unsubstituted heteroaryl.

Surprisingly it has been ascertained that in the case of the compounds of the invention, by the common structural element in the donor block Z, that at least one group M and one group N are each linked in such a way that at least one N atom of the group M and one O atom of the group N are joined to one another in each case via 2 C atoms, these compounds broadly and strongly absorb radiation, especially light, something which is able to lead to elevated efficiencies in organic photoactive components. Moreover, these compounds also have an enhanced charge carrier mobility, and so organic electronic components, such as transistors, which comprise the compounds of the invention are also able to exhibit improved electrical values.

The compounds of the invention may in particular also be used as charge carrier transport layers, e.g., p-conducting materials. The absorption spectrum and emission spectrum may extend starting from the lower UV through to the infrared spectral range.

The above-described at least one group M is selected from pyrrole structures or fused pyrrole scaffolds with at least one N atom, of the following general formulae 1 to 3:

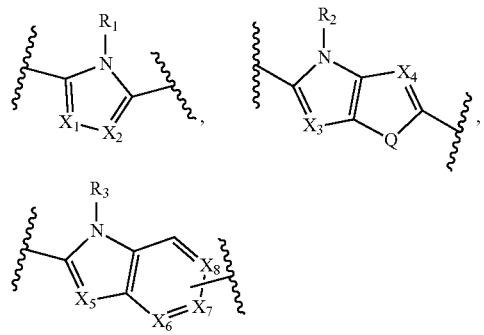

This group M is joined directly to at least one group N which is selected from furan structures or fused furan scaffolds having at least one O atom, of the following general formulae 3 to 5:

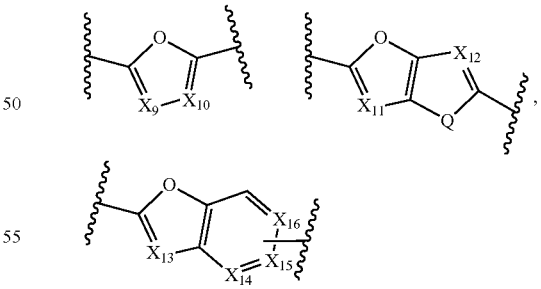

It is possible here that in the middle group Z there may also be a succession of a plurality of dual groups composed of M-N and/or N-M blocks if the parameter c is >1, e.g., *-M-N-M-N-M-N—*, *-M-N—N-M-M-N—* or *—N-M-N-M-N-M-N-M-*.

On the basis of this structural feature (*-M-N—*)$_c$ or (*—N-M-*)$_c$, the present compounds have a high optical density, preferably in the visible spectral range, and in particular a high integral over the optical density in the absorption spectrum in comparison to compounds not of the invention which do not have the above-described structural element. "Integral" here means the area content below a curve in the absorption spectrum, which is an important feature for the suitability of the material as an organic photosensitive material.

The present compounds of the invention of the general formula I may, in addition to the electron donor group Z which is always present, have further electron donor groups T1, T2, T3 and T4, which result in a further extension of the conjugated n-electron system already present through Z. The electron donor groups are flanked by terminal electron acceptor groups EWG1 and EWG2.

The compounds of the invention are, in particular, what are called "small molecules", by which are meant nonpolymeric, oligomeric, organic molecules having a molar mass between 100 to 2000 g/mol, which in particular may also be monodisperse.

The electron-withdrawing groups EWG1 and EWG2 may preferably independently of one another be selected from:

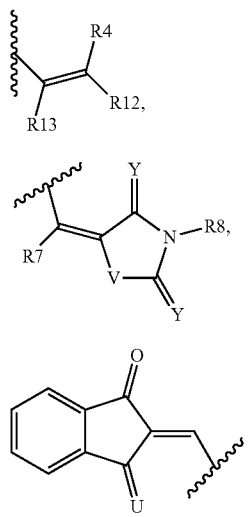

Formula 7

Formula 8

Formula 9 and $l$ designates the attachment to the groups T1 to T4 or Z in the compound of the general formula I, with $R_4$ and $R_{12}$ each independently of one another being selected from H, CN, COOR, with the proviso that $R_4$ and $R_{12}$ cannot both be H, where R is selected from the same group of compounds as defined in the case of $R_1$ to $R_3$, with each $R_{13}$ independently of any other being selected from a group: H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, where, if the substituent $R_5$ or $R_6$ is present in the compound of the formula I, a ring closure between $R_5$ with $R_{13}$ or $R_6$ with $R_{13}$ is possible, with the proviso that the double bond from formula 11 or formula 11* is located in each case between $R_5$ and $R_{13}$ or between $R_6$ and $R_{13}$, with V being O, S with Y being O, S, C(CN)$_2$ with U being O, S, C(CN)$_2$ with $R_7$ and $R_8$ each independently of one another being selected from a group H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, where for each of the groups EWG1 and EWG2, each independently of one another in each case for each C=C double bond, both the E-isomer and the Z-isomer may be present.

For each C=C double bond in the formulae 7, 8 and 9, therefore, both the E-isomer ("E"=German entgegen=contrary; i.e., trans configuration) and the Z-isomer ("Z"=German zusammen=together; i.e., cis configuration) may be present, these isomers being formed by an imaginary rotation by 180° about the axis of the C=C double bond. This will be explained below using as example the radical of the formula 8:

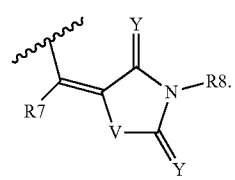

Both isomers, which may be present separately from one another, can be converted into one another by an imaginary rotation about the C=C double bond (indicated by the arrow on the double bond), thus resulting in the following two isomers for the group of the formula 8:

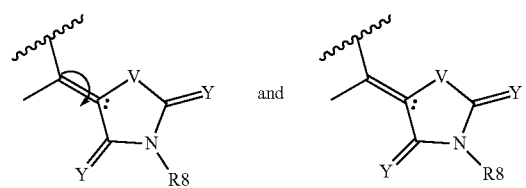

Furthermore, in particular, EWG1 may be the same as EWG2.

In the compounds of the invention of the general formula I, the aryl groups and the heteroaryl groups may preferably be $C_5$-$C_{10}$ aryl und $C_5$-$C_{10}$ heteroaryl groups. Substituents are understood to be all atoms and groups of atoms other than hydrogen. Substituents contemplated include, in particular, halogen, e.g., fluorine, or else $C_1$-$C_5$ alkyl groups, which may be substituted in turn. The O-alkyl, S-alkyl, O-alkenyl, S-alkenyl and alkynyl groups may each be $C_1$-$C_{20}$ groups, preferably $C_1$-$C_5$ groups.

The cyclic or open-chain $C_1$-$C_{20}$ alkyl groups of the compounds of the formula I of the invention may be linear or else branched and are preferably $C_1$-$C_5$ alkyl groups. Nonadjacent and nonterminal C atoms in these alkyl groups may be replaced by heteroatoms.

By "heteroatoms" in the sense of the present compounds of the formula I are meant, in particular, O, S, Se or NR'''', with the substituent R'''' being defined like the substituents $R_1$ to $R_3$ which have already been described above.

The bonding locations for the individual groups, which are designated by $l$, characterize the points of attachment of the respective groups to the other groups of the compounds of the formula I; in other words, for example, for the electron-withdrawing group EWG1 in the compound of the formula I, the attachment either to the donor groups T1 (for a=1) or T2 (for a=0 and b=1), or to the donor group Z if the parameters a and b are both 0.

These organic materials are applied in the form of thin films or in small volume to the foils by printing, bonding, coating, vapor deposition or otherwise. Methods contemplated for the production of the thin layers are also all those which are also used for electronics on glass, ceramic supports or semiconducting supports.

According to a further embodiment of the present invention, in the compounds of the formula I c=1 with the general formula

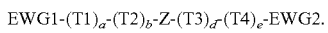

The inventors have ascertained that one donor block Z is sufficient to obtain an increased optical density relative to structurally different compounds.

Furthermore, the electron-withdrawing groups EWG1 and EWG2 may independently of one another be the following groups of the formula 7:

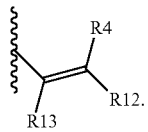

Electron-withdrawing groups EWG1 and EWG2 of this kind lead to oligomeric compounds of the formula I which can be applied particularly effectively by vapor deposition to substrates. With particular preference, $R_4$ and $R_{12}$ are CN, thus resulting in the particularly strongly electron-withdrawing group dicyano-vinylene. Moreover, the substituent $R_{13}$ may preferably be H.

According to a further embodiment of the present invention, the compounds of the formula I with c=1 of the general formula:

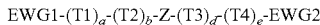

with Z=*-M-N—* or *—N-M-* have a group M of the formula 1:

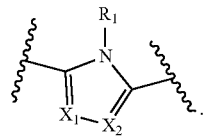

These simple pyrrole structural units for the donor block M, which have no further fused aromatic n-electron system, already lead to a marked increase in the absorption of radiation for the compounds of the invention when they also have the donor group N as well. It is, however, also possible to use fused ring systems as donor block M which contain pyrrole, such as indoles or other compounds covered by the general formulae 2 or 3, for example.

The terms "substituted" and "substituent" should be interpreted in the sense of the present invention to mean that one or more H atoms have been exchanged for any other group of atoms or another atom. "Substituents" in this sense may in particular be a halogen or a pseudo halogen, e.g., fluorine or CN, and also an aryl group, e.g., phenyl, or an alkyl group, e.g., a $C_1$-$C_6$ alkyl group.

The general groups and substituents in this donor block M of the general formula I may be defined as follows:
$X_1$ and $X_2$ independently of one another are selected from C—R with each R independently of any other selected from a group composed of H, halogen, branched or linear, cyclic or open-chain $C_1$-$C_{20}$ alkyl.
The further donor block N in structural fragment Z may be the following general group of the formula 4:

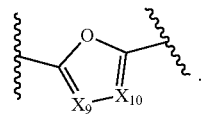

These simple furan structural units for the donor block N, which have no further fused aromatic n-electron system, already lead to a marked increase in the absorption of radiation for the compounds of the invention when they also have the donor group M as well. Also possible, however, is the use of fused donor blocks which receive furan, such as, for example, benzofurans or other compounds covered by the general formulae 5 or 6.

The general groups $X_9$ and $X_{10}$ in the formula 4 may preferably be selected, independently of one another, from C—R with each R independently of any other being selected from a group composed of H, halogen, branched or linear, cyclic or open-chain $C_1$-$C_{20}$ alkyl.

The conjugated π-electron system of the donor region of the compounds of the invention of the formula I may be expanded beyond the donor block Z by incorporation of at least one further donor block T1, T2, T3 or T4 and correspondingly by setting the parameters a, b, d or e associated with these donor blocks in the formula I successively to 1.

In particular, a may be 1, and in that case the group T1 may preferably be selected from the groups of the formulae 10 and/or 11:

Formula 10

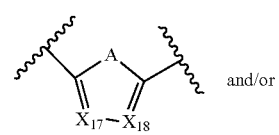

and/or

Formula 11

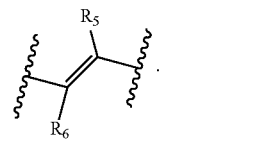

For the formula 10, the following in particular may apply: A=S or O.

Furthermore, in formula 10, $X_{17}$ and $X_{18}$ may be C—R, where R independently at each occurrence is selected from a group composed of H, halogen, branched or linear, cyclic or open-chain $C_1$-$C_{20}$ alkyl; $R_5$ and $R_6$ each independently of one another are selected from H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, where, if the substituent $R_5$ and $R_6$ is present in the compound, a ring closure between $R_5$ with $R_{13}$ and between $R_6$ with $R_{13}$ is possible, with the proviso that the double bond from formula 11 or formula 11* is located between $R_5$ and $R_{13}$ or between $R_6$ and $R_{13}$.

If the donor block T2 is present, b is 1, and T2 is preferably the general group of the formula 10

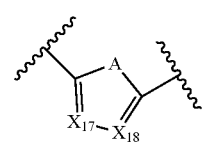

In the formula 10, preferably A is S or O. Moreover, in the formula 10, $X_{17}$ and $X_{18}$ may be C—R, where R independently at each occurrence is selected from a group composed of H, halogen, branched or linear, cyclic or open-chain $C_1$-$C_{20}$ alkyl.

When the donor block T3 is present, d is 1, and the group T3 is preferably selected from the groups of the formulae 10 or 11:

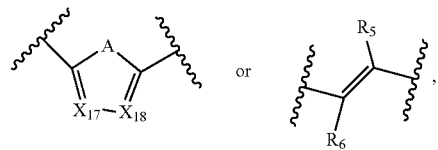

where for the formula 10 the following may be the case: A=S or O.

In the formula 10, in particular, $X_{17}$ and $X_{18}$ may be C—R, where R independently at each occurrence is selected from a group composed of H, halogen, branched or linear, cyclic or open-chain $C_1$-$C_{20}$ alkyl, $R_5$ and $R_6$ each independently of one another are selected from H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, where, if the substituent $R_5$ and $R_6$ is present in the compound, a ring closure between $R_5$ with $R_{13}$ or $R_6$ with $R_{13}$ is possible, with the proviso that the double bond from formula 11 or formula 11* is located between $R_5$ and $R_{13}$ or between $R_6$ and $R_{13}$.

Analogously to T3, T4 with e=1 may also preferably be selected from the groups of the formulae 10 or 11, in which case the general groups and substituents for these formulae are preferably selected exactly the same as for T3.

The inventors have ascertained that through the presence in particular of a further heterocyclic group, which may be a furan or a thiophene residue, and also of double bonds which are preferably located adjacent to at least one of the electron-withdrawing groups EWG1 and/or EWG2, but may also be located between a heterocyclic group and the central donor block Z, it is possible to prepare further molecules of the invention which possess the advantageous properties already stated.

Furthermore, the double bonds (formula 11 or formula 11*) may also be present adjacent to both electron-withdrawing groups EWG1 and EWG2.

Also possible is a ring closure between the group $R_5$ of the formula 11 or formula 11* with the group $R_{13}$ of the formula 7 of the electron-withdrawing groups EWG1 and/or EWG2, or else between the group $R_6$ of the formula 11 or formula 11* with $R_{13}$ of the formula 7, with the proviso that the double bond from formula 11 is located between $R_5$ and $R_{13}$ or between $R_6$ and $R_{13}$, with the ring closure being present in particular in the form of an optionally substituted cyclopentenyl ring or of an optionally substituted cyclohexenyl ring (see, for example, the inventive compounds 1 and 2 in table 1).

In a further embodiment of the present invention, the compounds of the invention have particular preferred donor blocks for the groups Z and T1 to T4, so resulting in a general structural formula II:

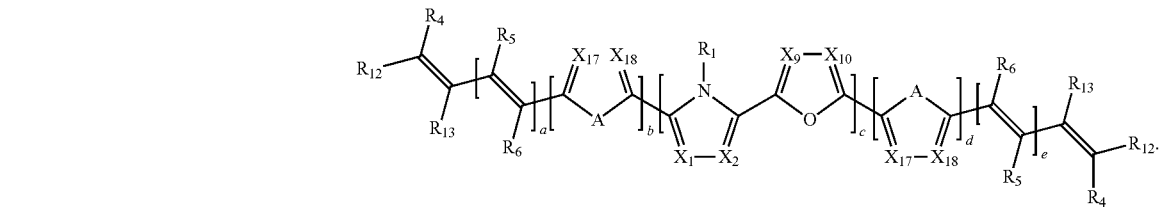

The substituents and general groups here may be defined in the manner described already. Preference here is given to the following definitions for the formula II, although in a most general form the definitions valid for the substituents and the general groups are those defined for the compounds of the formula I:

A is O or S, independently of one another $X_{17}$, $X_{18}$, $X_1$, $X_2$, $X_9$ and $X_{10}$ are C—R, where R independently at each occurrence is selected from a group composed of H, halogen, branched or linear, cyclic or open-chain $C_1$-$C_{20}$ alkyl, $R_5$ and $R_6$ each independently of one another are selected from H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, and where, if the substituents $R_5$ and $R_6$ are present, they may form a ring closure between $R_5$ with $R_{13}$ or $R_6$ with $R_{13}$, at least one of the parameters a, b, d or e is 1, and it is also possible for all of these parameters to be 1; preferably at least one of the parameters is 0, e.g., T4, while all other parameters are 1, $R_4$ and $R_{12}$ each independently of one another are selected from H and CN, with the proviso that $R_4$ and $R_{12}$ cannot both be H.

In a further aspect of the present invention, all of the compounds of the invention described above can be used in an organic electronic component.

In view of the particularly strong absorption of the compounds of the invention, excitons are formed to particularly good effect in layers which comprise these compounds, thus leading, in organic photoactive components comprising these compounds, to higher fill factors FF, improved open-circuit voltage $V_{oc}$, and improved short-circuit current density $J_{sc}$. With other organic electronic devices, better electronic values are likewise to be expected in view of the elevated charge carrier transport properties of the compounds of the invention.

The term "organic electronic component" refers to all electronic components which can be produced using organic conducting or semiconducting materials, examples being transistors, such as organic field-effect transistors, organic light-emitting components, organic photoactive devices in which excitons (electron-hole pairs) can be formed in a photoactive layer by irradiation, such as photodetectors, for example, or organic solar cells.

These organic electronic components generally have an electrode and a counterelectrode, with an organic functional layer arranged between them. This organic functional layer may exert a function important for the electronic operation of the organic component, such as a charge carrier transport function, such as the transport of holes (p-conducting) or the transport of electrons (n-conducting). Furthermore, the organic functional layer may also comprise a light-emitting layer which emits radiation, light for example, when a voltage is applied to the electrode and counterelectrode, through recombination of the holes (positive charges) and electrodes (negative charge). The organic functional layer may also be a photoactive layer in which excitons (electron-hole pairs) are formed on irradiation with a form of radiation, light for example, or else UV radiation or IR radiation. With organic photoactive layers, what are called planar heterojunctions may be formed, in particular, in which a planar, p-conducting layer is adjacent to a planar, n-conducting layer and the excitons formed by irradiation either in the p-conducting or the n-conducting layer can be separated into holes and electrons at the interface between the two layers. Furthermore, the photoactive layer may also comprise what is called a bulk heterojunction, where p-conducting and n-conducting materials transition into one another in the form of an interpenetrating network, where again the separation of the excitons formed by irradiation occurs at the interfaces between p-conducting and n-conducting materials.

Excitons are electrically neutral excitation states, the electron-hole pairs, which are then separated into electrons and holes in a further step at a p-n junction. Separation takes place accordingly into free charge carriers, which contribute to electrical current flow. A limiting factor here is the size of the bandgap of the semiconductor; accordingly, the only photons which can be absorbed are those having an energy which is greater than its bandgap. Light always only generates excitons, not free charge carriers, and hence the low-recombination diffusion is an important component for the level of the photocurrent. The exciton diffusion length here must exceed the typical depth of penetration of the light, so that as large a portion of the light as possible can be utilized electrically.

A construction already known from the literature for a common organic solar cell is composed of a pin or nip diode [Martin Pfeiffer, "Controlled doping of organic vacuum deposited dye layers: basics and applications", PhD thesis TU Dresden, 1999 and WO2011/161108A1]: a pin solar cell consists of a carrier/substrate followed by a usually transparent base contact, p-layer(s), i-layer(s), n-layer(s), and a top contact. A nip solar cell consists of a carrier/substrate followed by a usually transparent base contact, n-layer(s), i-layer(s), p-layer(s) and a top contact.

Here, n and p doping, respectively, mean doping leading to an increase in the density of free electrons and holes, respectively, in the thermal equilibrium state. Such layers are therefore to be understood primarily as transport layers. It is also possible for n- or p-layer(s) to be at least partly nominally undoped and to possess preferably n-conducting or p-conducting properties solely on the basis of the physical properties (e.g., different mobility) or on the basis of different impurities (e.g., residues from the synthesis or from layer production) or as a result of environment effects (e.g., bordering layers, inward diffusion of metals or other organic materials, gas doping from the surrounding atmosphere). In this sense, such layers should be understood preferably as transport layers.

The excitons pass by diffusion to an interface of this kind where electrons and holes are separated from one another. The material which accepts the electrons is referred to as the acceptor, and the material which accepts the holes is referred to as the donor.

The designation "i-layer" marks out an undoped or intrinsic layer. One or more i-layers here may consist of one material (planar heterojunctions) or else of a mixture of two or more materials, referred to as bulk heterojunctions, which have an interpenetrating network.

Also known from the literature are organic pin tandem cells and pin multiple cells (DE 10 2004 014 046). WO 2011 161 108 A1 discloses in this regard a proposal for realization in the form of a photoactive component having an electrode and a counterelectrode, there being at least one organic layer system arranged between the electrodes, and also having at least two photoactive layer systems and, between the photoactive layer systems, at least two different transport layer systems of the same charge carrier type, characterized in that a transport layer system is adapted energetically to one of the two photoactive layer systems and the other transport layer system is implemented transparently.

The organic electronic components may also comprise further metal oxide layers.

Table 1, in an overview, shows the structures, melting points, and absorption maximum (in nm and eV in the solvent (SV)) of exemplary embodiments of inventive compounds covered by both the general formulae I and II. The synthesis of these compounds is elucidated in detail additionally later on below.

TABLE 1

| Number | Structure | M.p./°C.[a] | λmax (SV)/nm[b] | λmax (SV)/eV[b] |
|---|---|---|---|---|
| 1 | (chemical structure) | 290 | 528 | 2.35 |

TABLE 1-continued

| Number | Structure | M.p./° C.[a] | λmax (SV)/nm[b] | λmax (SV)/eV[b] |
|---|---|---|---|---|
| 2 | 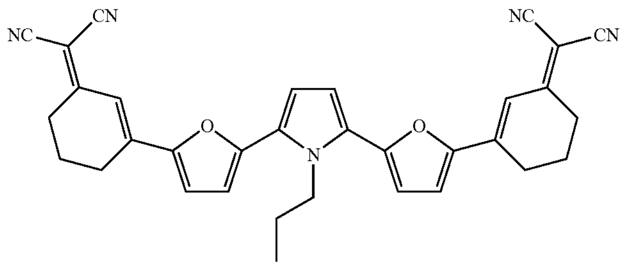 [SMILES: CCCn1c(-c2ccc(C3=CC(=C(C#N)C#N)CCC3)o2)ccc1-c1ccc(C2=CC(=C(C#N)C#N)CCC2)o1] | 292 | 544 | 2.28 |
| 3 | 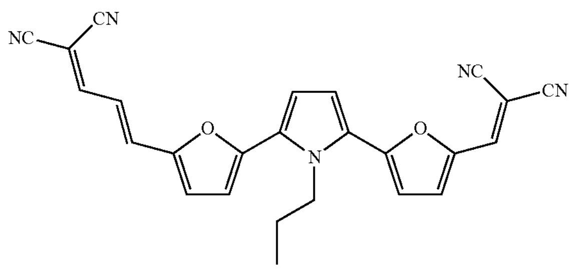 [SMILES: CCCn1c(-c2ccc(C=C(C#N)C#N)o2)ccc1-c1ccc(/C=C/C=C(C#N)C#N)o1] | 224 | 555 | 2.23 |
| 4 | 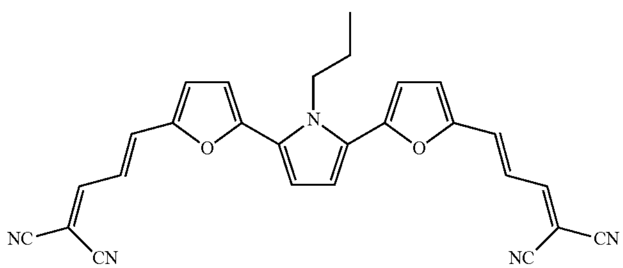 [SMILES: CCCn1c(-c2ccc(/C=C/C=C(C#N)C#N)o2)ccc1-c1ccc(/C=C/C=C(C#N)C#N)o1] | 261 | 590 | 2.10 |
| 5 | 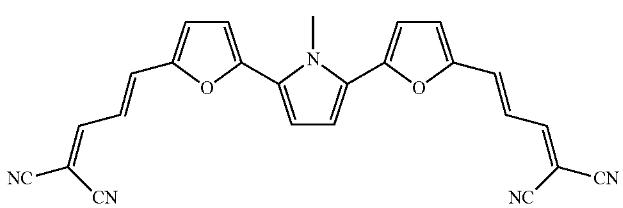 [SMILES: Cn1c(-c2ccc(/C=C/C=C(C#N)C#N)o2)ccc1-c1ccc(/C=C/C=C(C#N)C#N)o1] | 231 | 575 | 2.16 |
| 6 | 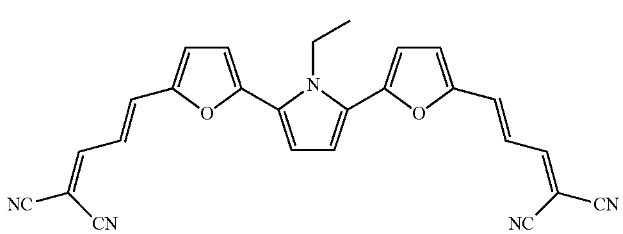 [SMILES: CCn1c(-c2ccc(/C=C/C=C(C#N)C#N)o2)ccc1-c1ccc(/C=C/C=C(C#N)C#N)o1] | 263 | 596 | 2.08 |
| 7 | 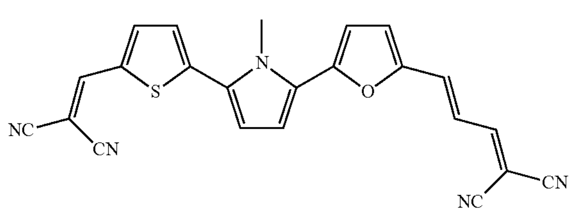 [SMILES: Cn1c(-c2ccc(/C=C/C=C(C#N)C#N)o2)ccc1-c1ccc(C=C(C#N)C#N)s1] | 265 | 543 | 2.28 |

TABLE 1-continued

| Number | Structure | M.p./° C.[a] | λmax (SV)/nm[b] | λmax (SV)/eV[b] |
|---|---|---|---|---|
| 8 | 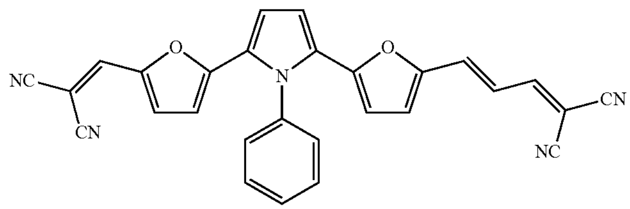 [SMILES: N#CC(C#N)=C/C=C/c1ccc(-c2ccc(-c3ccc(C=C(C#N)C#N)o3)n2-c2ccccc2)o1] | 254 | 566 | 2.19 |
| 9 | 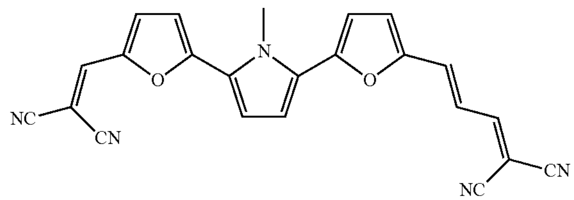 [SMILES: Cn1c(-c2ccc(C=C(C#N)C#N)o2)ccc1-c1ccc(/C=C/C=C(C#N)C#N)o1] | 246 | 553 | 2.24 |
| 10 | 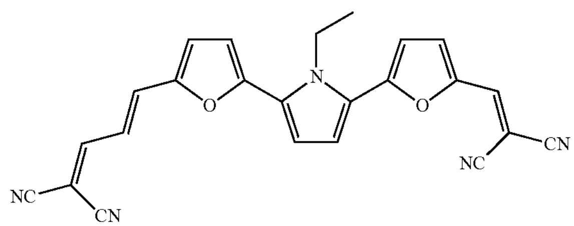 [SMILES: CCn1c(-c2ccc(C=C(C#N)C#N)o2)ccc1-c1ccc(/C=C/C=C(C#N)C#N)o1] | 245 | 568 | 2.18 |
| 11 | 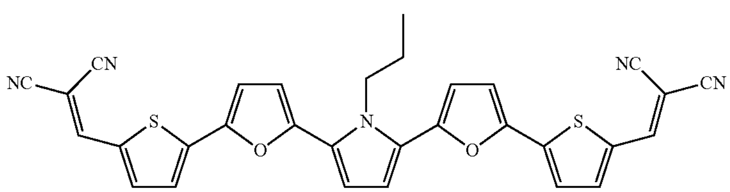 [SMILES: CCCn1c(-c2ccc(-c3ccc(C=C(C#N)C#N)s3)o2)ccc1-c1ccc(-c2ccc(C=C(C#N)C#N)s2)o1] | 243 | 542 | 2.28 |
| 12 | 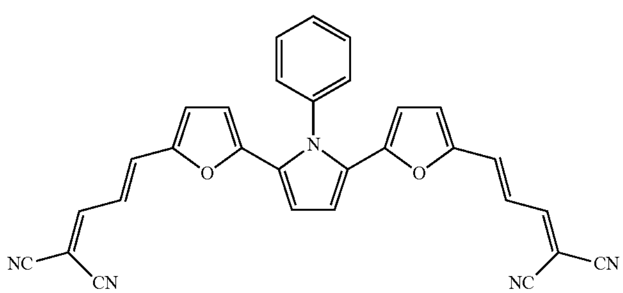 [SMILES: N#CC(C#N)=C/C=C/c1ccc(-c2ccc(-c3ccc(/C=C/C=C(C#N)C#N)o3)n2-c2ccccc2)o1] | 279 | 596 | 2.09 |
| 13 | 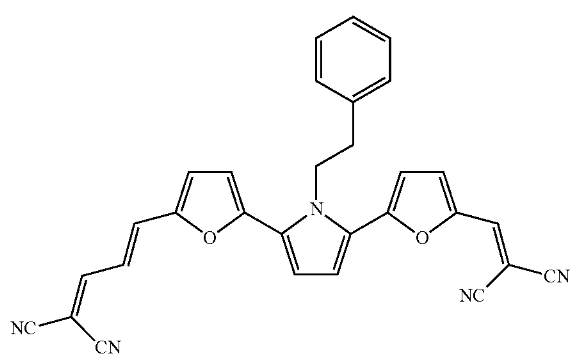 [SMILES: N#CC(C#N)=C/C=C/c1ccc(-c2ccc(-c3ccc(C=C(C#N)C#N)o3)n2CCc2ccccc2)o1] | 206 | 550 | 2.26 |

TABLE 1-continued

| Number | Structure | M.p./° C.[a] | λmax (SV)/nm[b] | λmax (SV)/eV[b] |
| --- | --- | --- | --- | --- |
| 14 | 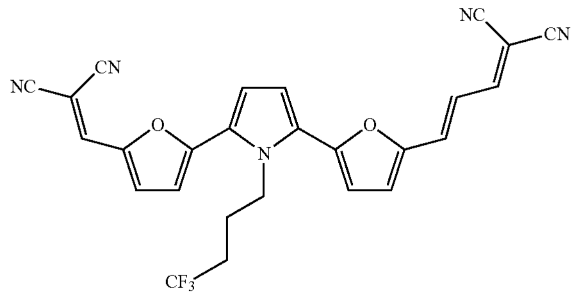 [SMILES: N#CC(C#N)=C/C=C/c1ccc(-c2ccc(-c3ccc(C=C(C#N)C#N)o3)n2CCCC(F)(F)F)o1] | 212 | 547 | 2.27 |
| 15 | 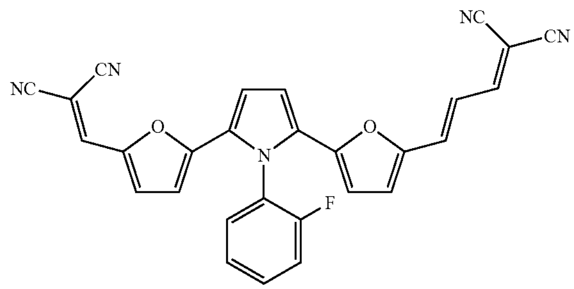 [SMILES: N#CC(C#N)=C/C=C/c1ccc(-c2ccc(-c3ccc(C=C(C#N)C#N)o3)n2-c2ccccc2F)o1] | 255 | 543 | 2.29 |
| 16 | 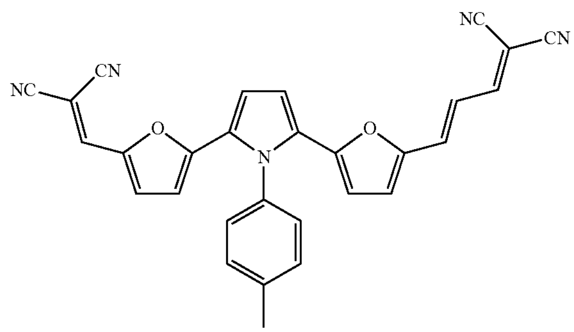 [SMILES: Cc1ccc(-n2c(-c3ccc(C=C(C#N)C#N)o3)ccc2-c2ccc(/C=C/C=C(C#N)C#N)o2)cc1] | 292 | 568 | 2.19 |
| 17 | 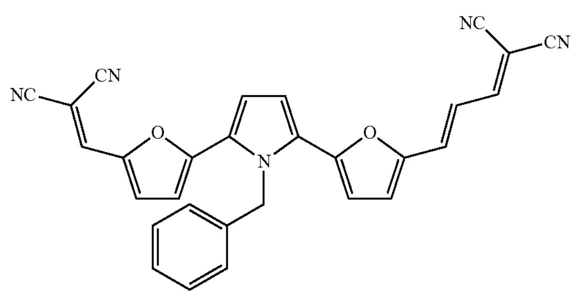 [SMILES: N#CC(C#N)=C/C=C/c1ccc(-c2ccc(-c3ccc(C=C(C#N)C#N)o3)n2Cc2ccccc2)o1] | 264 | 543 | 2.29 |
| 18 | 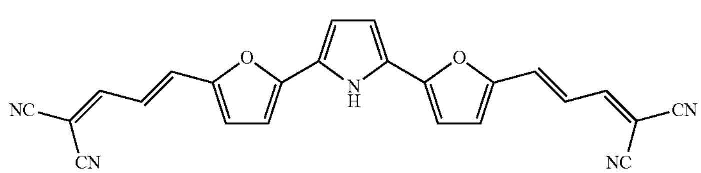 [SMILES: N#CC(C#N)=C/C=C/c1ccc(-c2ccc(-c3ccc(/C=C/C=C(C#N)C#N)o3)[nH]2)o1] | 270 | 595 | 2.09 |
| 19 | 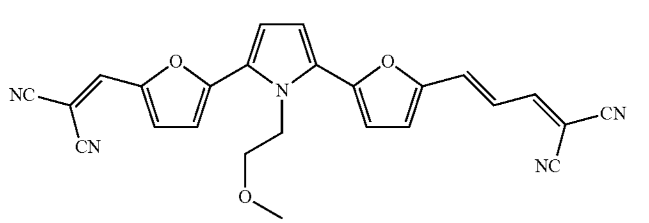 [SMILES: COCCn1c(-c2ccc(C=C(C#N)C#N)o2)ccc1-c1ccc(/C=C/C=C(C#N)C#N)o1] | 199 | 543 | 2.29 |

TABLE 1-continued

| Number | Structure | M.p./° C.[a] | λmax (SV)/nm[b] | λmax (SV)/eV[b] |
|---|---|---|---|---|
| 20 | 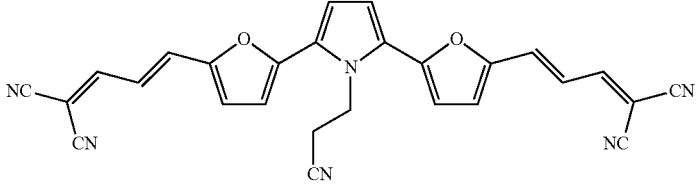 [SMILES: N#CCCn1c(-c2ccc(/C=C/C=C(C#N)C#N)o2)ccc1-c1ccc(/C=C/C=C(C#N)C#N)o1] | not det. | not det. | not det. |
| 21 | 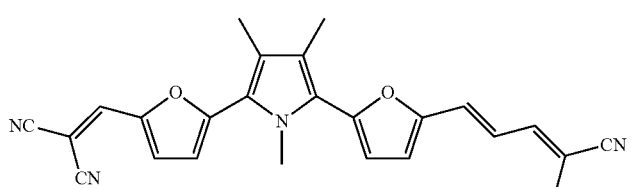 | not det. | not det. | not det. |
| 22 | 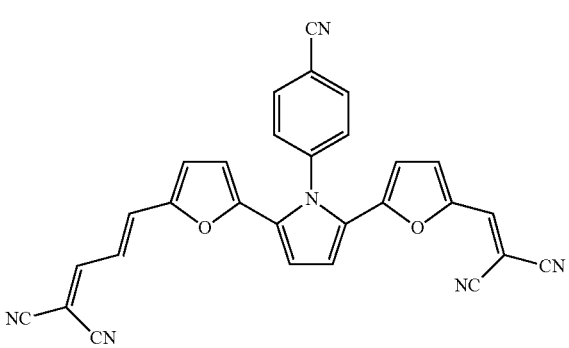 [SMILES: N#CC(C#N)=C/C=C/c1ccc(-c2ccc(-c3ccc(C=C(C#N)C#N)o3)n2-c2ccc(C#N)cc2)o1] | 279 | 529 | 2.35 |

[a]Onset DSC (differential scanning calorimetry; start of melting range; extrapolated initial temperature (intersection of inflection tangent and baseline)
[b]In dichloromethane unless otherwise noted Surprisingly it has been found that the inventive compounds exhibit particularly strong absorption (i.e., high optical density at the absorption maximum or high integral over the optical density in the visible spectral range in comparison to similar compounds outside the range claimed here).

In this context, FIG. 1 shows a comparison of the absorption spectra (optical density over wavelength in nm) for vacuum-deposited films 30 nm thick, for the inventive compounds 4 and 10 of table 1 in comparison to two noninventive compounds: comparative material 1 and comparative material 2.

The structures and scientific publications relating to the syntheses of the two comparative materials are as follows:
Comparative material 1:

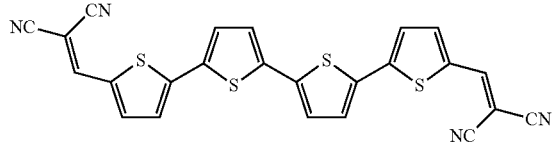 [SMILES: N#CC(C#N)=Cc1ccc(-c2ccc(-c3ccc(-c4ccc(C=C(C#N)C#N)s4)s3)s2)s1]

(Fitzner et al., Adv. Funct. Mat. 2011, 21, 897-910)
Comparative material 2:

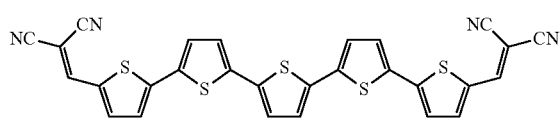 [SMILES: N#CC(C#N)=Cc1ccc(-c2ccc(-c3ccc(-c4ccc(-c5ccc(C=C(C#N)C#N)s5)s4)s3)s2)s1]

(Fitzner et al., Adv. Funct. Mat. 2011, 21, 897-910).

From the absorption spectra of FIG. 1 it can be seen that the inventive compounds absorb radiation to a substantially greater extent than the comparative compounds, and therefore have a higher optical integral over the optical density in the visible spectral range.

The advantageous synergistic effect of inventive compounds which comprise EWG1 and EWG2 groups in interaction with a donor block comprising a furan unit directly alongside a pyrrole unit is also apparent from the following, very direct comparison of the inventive compounds 7, 9 and 10 of table 1 with the comparative compound 3 having the following structure:

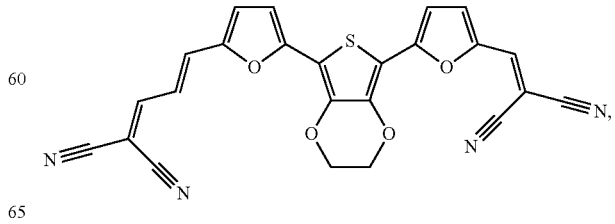

which contains an EDOT group instead of pyrrole.

Table 2 below shows various parameters of this series of materials in direct comparison. The photovoltaic parameters $V_{oc}$, $J_{sc}$ and FF relate in each case to solar cells with a mixed layer, 30 nm thick, of the respective donor material of these compounds and fullerene C60 as photoactive layer on glass, with a construction of ITO/C60 (15 nm)/the respective compounds:C60 (30 nm)/BPAPF (10 nm)/BPAPF:NDP9 (30 nm)/NDP9 (1 nm)/Au (50 nm), measured under AM1.5 illumination (Am=Air Mass; AM=1.5 for this spectrum amounts to the overall radiant power 1000 W/m²; AM=1.5 as standard value for the measurement of solar modules). ITO here serves as an anode, and the adjacent fullerene C60 serves as an electron transport layer ETL, being followed by the photoactive layer as bulk heterojunction between C60 as electron acceptor material and the respective compound as hole acceptor material (donor material), followed by BPAPF (9,9-bis[4-(N,N-bis-biphenyl-4-yl-amino)phenyl]-9H-fluorene) as hole transport layer HTL and by BPAPF doped with NDP9 (Novaled AG), followed by an Au cathode.

Figure 2:
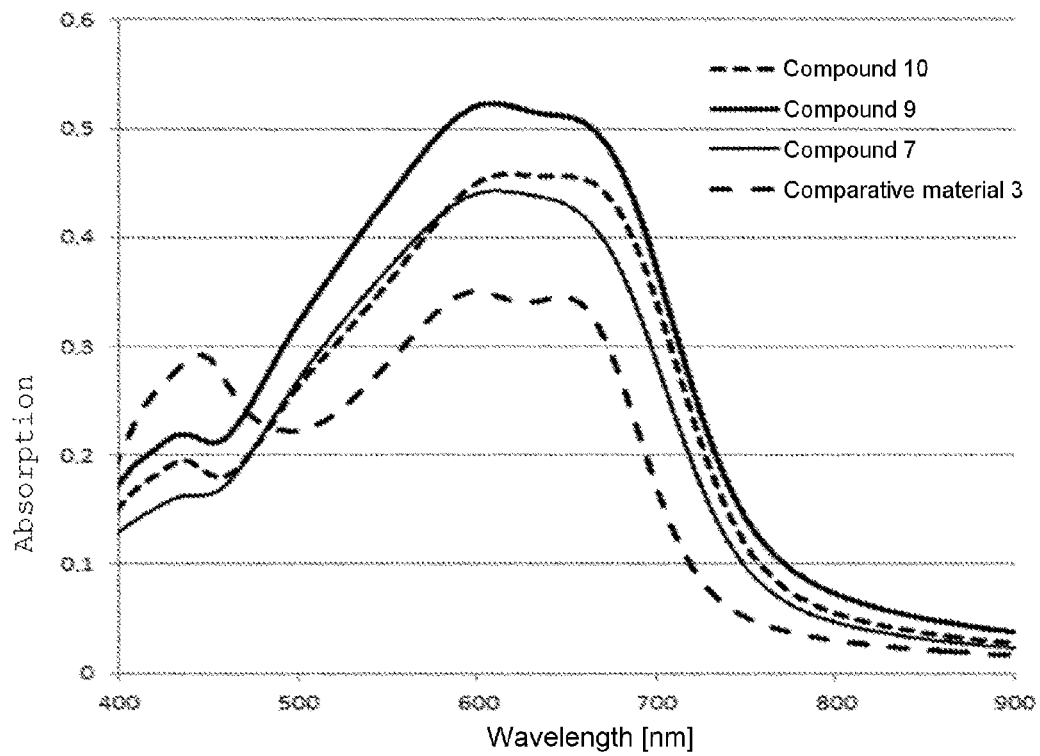

The spectral data of FIG. 2 show the absorption spectra of comparative material 3 in comparison with inventive compounds 7, 9 and 10. The data relate to layers 30 nm thick applied by vacuum deposition to fused silica, and show that the inventive compounds have a higher optical integral over the optical density in the visible spectral range than noninventive compounds of similar structure.

Table 2 shows the optical density at the absorption maximum (ODmax), the optical integral in the visible range (OD-integral), and also $V_{oc}$, $J_{sc}$, FF, and the efficiency:

TABLE 2

| Substance | ODmax | OD-integral (400-900 nm) [nm] | $V_{oc}$ [V] | $J_{sc}$ [mA/cm²] | FF [%] | eff [%] |
|---|---|---|---|---|---|---|
| Compound 10 (values in parentheses for cell with optimally adapted hole transport material) | 0.45 | 111/237 | 0.91 (0.91) | 14.6 (14.9) | 70.8 (73.4) | 9.4 (10.0) |
| Compound 9 | 0.53 | 130/242 | 0.91 | 13.2 | 71.3 | 8.6 |
| Compound 7 | 0.44 | 105/232 | 0.94 | 11.7 | 59.3 | 6.5 |
| Comparative compound 3 | 0.35 | 88/307 | 0.91 | 11.5 | 59.1 | 6.2 |

Independently of the substituent, compound 10 exhibits not only higher absorption maxima but also a significantly greater integral absorption in the visible range, although the donor strengths of pyrrole and EDOT are very similar. The superior properties of the inventive substances (compounds 9 and 10) in comparison to comparative material 3 are evident also, with an identical solar cell construction, in the photovoltaic parameters of fill factor (70%-73% for compounds 9 and 10 versus 59% for comparative material 3 with in each case photoactive layers 30 nm thick) and photocurrent $J_{sc}$ (13.2-14.9 mA/cm² for compounds 9 and 10 versus 11.5 mA/cm² for comparative compound 3). The significantly increased FF suggests that the compounds 9 and 10 have not only improved absorption properties but also superior charge carrier transport properties. Impressive evidence of the unusual transport properties of the class of substance claimed in accordance with the invention is the very high fill factor of 73% found for compound 10, despite the fact that compound 10 is a very short oligomer which comprises one double bond less than comparative material 1 and three double bonds less than comparative material 2.

Even the inventive compound 7 is still on an advantageous trend relative to the comparative compound 3, despite the significant drop it suffers as a result of the steric hindrance in direct vicinity between thiophene and pyrrole relative to the optimized compounds 9 and 10 (with furan on both sides of the pyrrole).

In a similar way, the advantages of the inventive substances are apparent in a further series of directly comparable, in this case mirror-symmetrical materials, which each have in common certain structural elements with the inventive compound 4 of table 1:

Comparative Material 4:

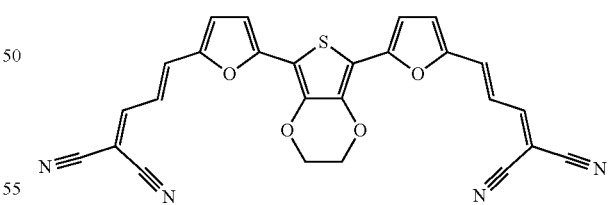

Comparative Material 5:

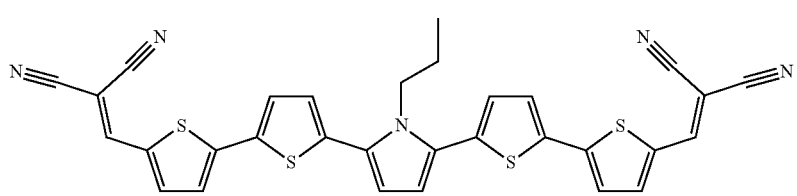 [SMILES: CCCn1c(-c2ccc(-c3ccc(C=C(C#N)C#N)s3)s2)ccc1-c1ccc(-c2ccc(C=C(C#N)C#N)s2)s1]

Comparative Material 6:

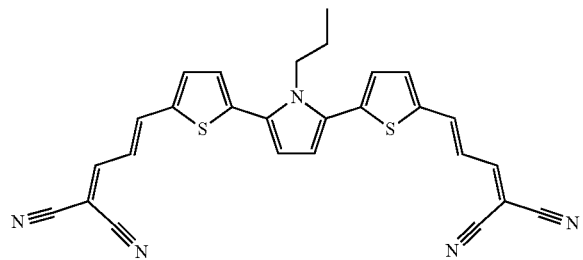 [SMILES: CCCn1c(-c2ccc(/C=C/C=C(C#N)C#N)s2)ccc1-c1ccc(/C=C/C=C(C#N)C#N)s1]

Figure 3:
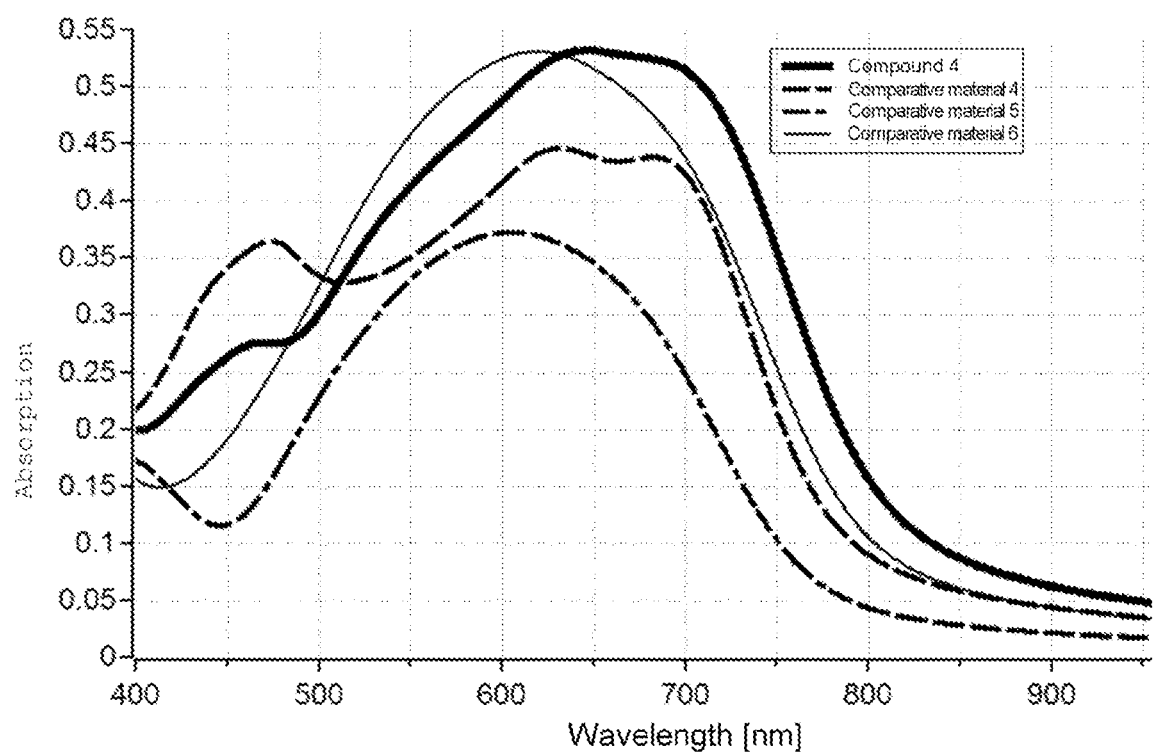

The absorption spectra of the materials are shown in FIG. 3. The spectral data relate to layers 30 nm thick applied by vacuum deposition to fused silica.

Table 3 below shows various parameters of this series of materials in direct comparison. The photovoltaic parameters $V_{oc}$, $J_{sc}$ and FF relate in each case to solar cells having a mixed layer 30 nm thick and composed of the respective donor material and fullerene C60 as photoactive layer on glass, with a construction of ITO/C60 (15 nm)/corresponding compound:C60 (30 nm)/HTM81 (10 nm)/HTM81:NDP9 (30 nm)/NDP9 (1 nm)/Au (50 nm), measured under AM1.5 illumination. The spectral data are based on layers 30 nm thick applied by vacuum deposition to fused silica.

TABLE 3

| Substance | ODmax | OD-integral (400-900 nm) [nm] | Voc [V] | Jsc [mA/cm²] | FF [%] | eff [%] |
|---|---|---|---|---|---|---|
| Compound 4 | 0.53 | 156 | 0.81 | 13.3 | 67.4 | 7.3 |
| Compound 6 | 0.4* | 114* | 0.81 | 15.1 | 69.7 | 8.5 |
| Comparative material 4 | 0.45 | 134 | 0.82 | 12.3 | 66.5 | 6.7 |
| Comparative material 5 | 0.37 | 91 | 0.88 | 10.4 | 57.4 | 5.3 |
| Comparative material 6 | 0.52 | 127 | 0.9 | 10.4 | 43.1 | 4.0 |

*Compound 6 exhibits severe tendency toward crystallization, thereby clouding the strong absorption in pure layers on glass. Mixed layers with fullerene C60 are less rough and display the expectedly strong absorption, which is manifested in the unusually high Jsc value for the solar cell based on the mixed layer.

Table 3 shows first of all that none of the comparative substances has an absorption integral at a similarly high level as compound 4. The closest in this connection is the closely structurally related comparative compound 6; the latter, however, has a much narrower and less structured spectrum, a fact probably attributable to a lower tendency toward self-organization, i.e., less-ordered layers (steric hindrance between pyrrole and thiophene), a phenomenon manifested drastically in the very much lower fill factor of the solar cell. Similar comments also apply to comparative compound 5, which, however, displays very much weaker absorption. Comparative material 4 with EDOT in place of the inventive pyrrole unit also drops off significantly in key parameters relative to compound 4—similarly, as shown above, to comparative material 3 in relation to compound 10.

It has also been possible to show that numerous derivatives of the inventive compounds are able not only to absorb light but also to be vacuum vapor-deposited without residue, whereas, for example, the comparative compound 6 shown above (with thiophene instead of furan as in compound 4) has a large decomposed residue in the vaporizer source.

Through very good charge transport properties and good absorption properties (see above) it is possible to generate high photocurrents with excellent fill factors. Accordingly it is possible to produce very well-combined tandem/triple/quadruple or multiple junction solar cells.

Figure 4:
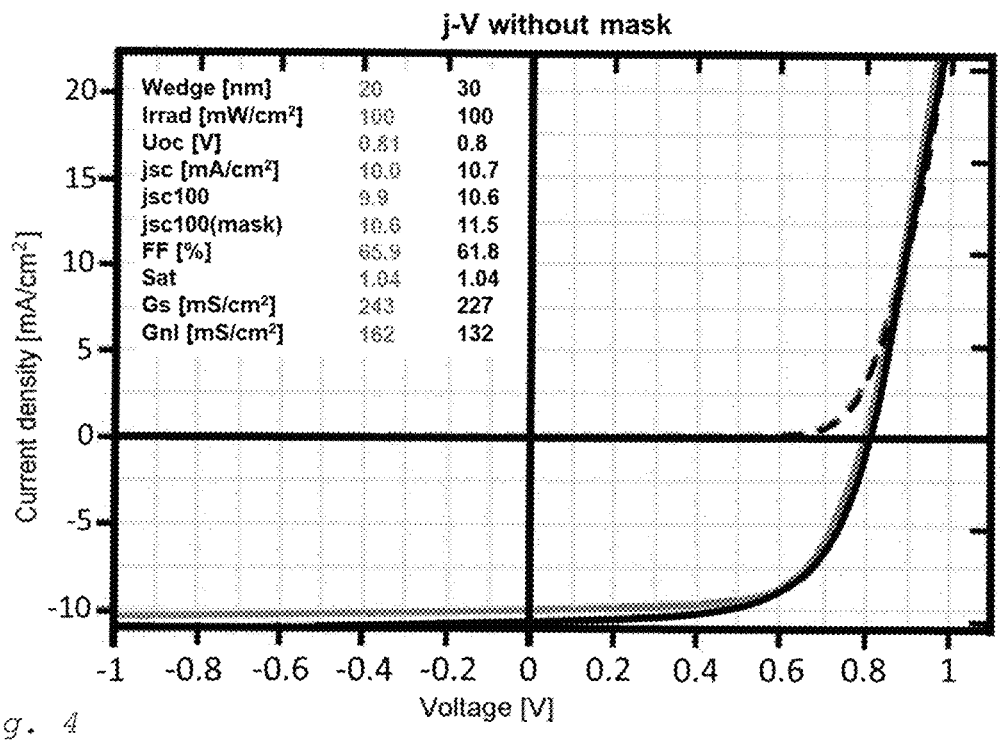
FIGS. 4 to 6 show current-voltage curves of organic photoactive components (solar cells) which include compounds of the present invention.

FIG. 4 shows the current-voltage curve with a BHJ cell having the following construction: ITO/C60 (15 nm)/compound 4:C60 (20/30 nm, 1:1, 70° C.)/BPAPF (10 nm)/BPAPF:NDP9 (30 nm, 9.1% wt)/NDP9 (1 nm)/Au (50 nm), the photoactive layer being a bulk heterojunction (BHJ).

Figure 5:
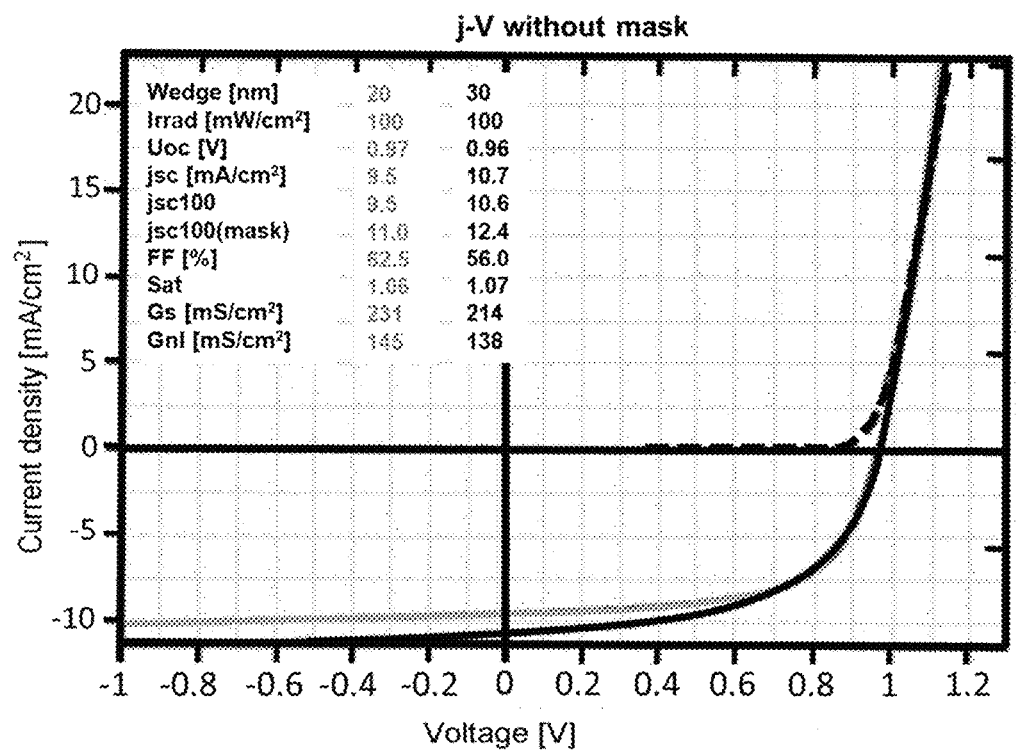

FIG. 5 shows the current-voltage curve with a BHJ cell having the following construction: ITO/C60 (15 nm)/compound 8:C60 (20/30 nm, 3:2, 70° C.)/BPAPF (10 nm)/BPAPF:NDP9 (30 nm, 9.7% wt)/NDP9 (1 nm)/Au (50 nm), the photoactive layer being a bulk heterojunction (BHJ).

Figure 6:
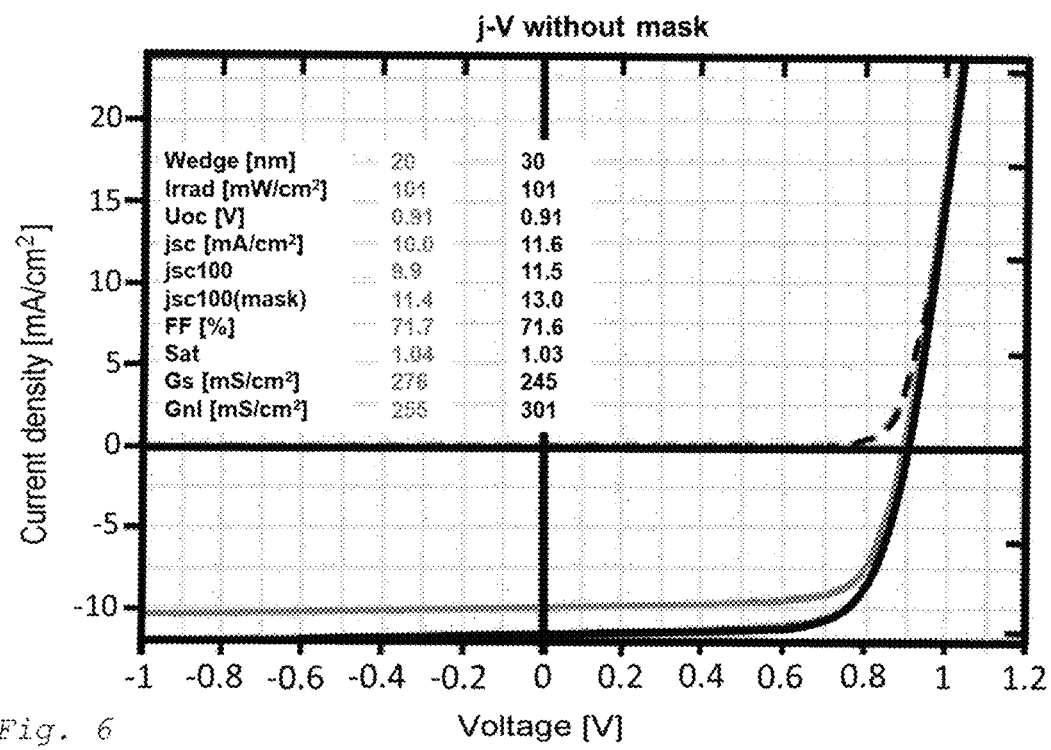

FIG. 6 shows the current-voltage curve with a BHJ cell having the following construction: ITO/C60 (15 nm)/compound 10:C60 (20/30 nm, 3:2, 50° C.)/BPAPF (10 nm)/BPAPF:NDP9 (30 nm, 10.6% wt)/NDP9 (1 nm)/Au (50 nm), the photoactive layer being a bulk heterojunction (BHJ).

Figure 7:
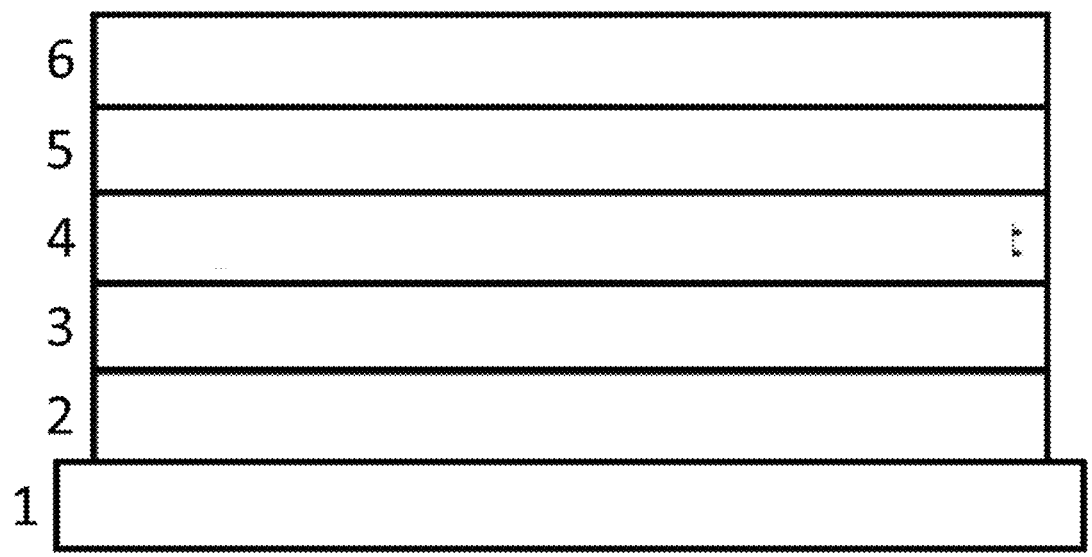
FIG. 7 shows an exemplary organic photoactive component in cross section.
Figure 8:
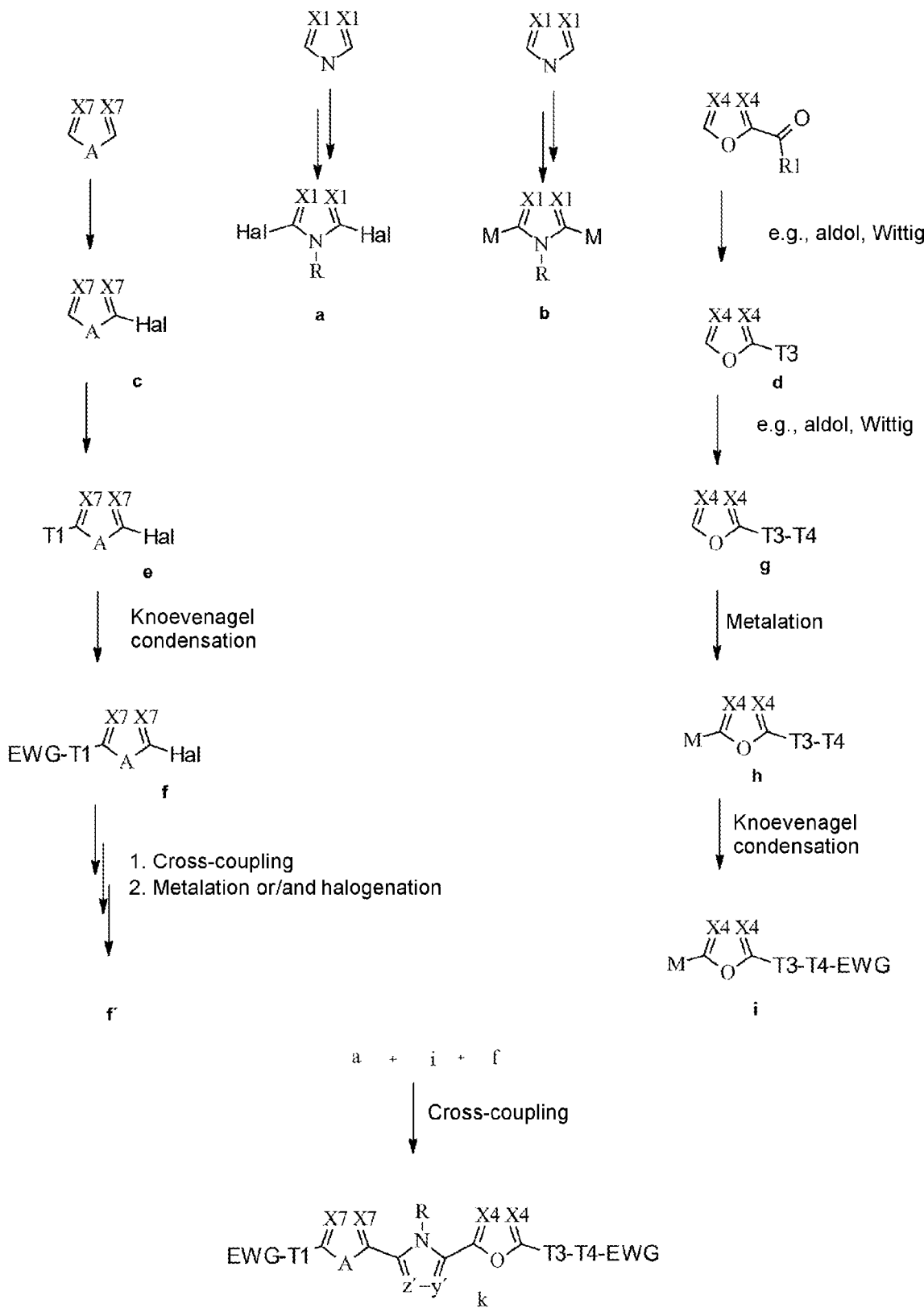
FIG. 8 shows an overview of the synthesis of inventive compounds.

FIG. 7 shows an exemplary photoactive device with a substrate 1, made of glass, for example, on which there is a cathode as electrode 2, which may comprise ITO, for example. Arranged thereon are an electron-transporting layer 3 as ETL and also a photoactive layer 4, comprising the inventive compounds as p-conducting donor component and, additionally, an n-conducting component as electron acceptor component, e.g., C60, either as a planar heterojunction or as a bulk heterojunction. Arranged above these is a hole-conducting layer 5 as HTL, and the anode 6.

Photoactive components with the compounds of the invention may comprise further functional layers and may for example also be designed as multiple cells or tandem cells.

In the text below, the syntheses of the specific exemplary embodiments, and a general synthesis pathway according to the modular system for the inventive compounds, will additionally be elucidated.

Synthesis

The absorber molecules of the invention can advantageously be made available easily and in good yields according to a simple modular system. Depicted below by way of example is the synthesis of the inventive compound of the general formula (I).

The general compound (I) can be synthesized according to one of the methods described below. This synthesis is intended to act here as an exemplary representation, and may be varied in the sequence of its individual steps, or modified by other known methods. The amalgamation of individual reaction steps, or the alteration to parts of the synthesis route, is also possible.

The substituent "Hal-" stands for halogen component, typically comprising a halogen atom, or else other functional groups which can be used in cross-coupling reactions, such as, for example, carboxylic acids or triflates, or further suitable groups including —H.

The substituent "Met-" stands for metal component, referring in the wider sense to metal-containing or semi-metal-containing functional groups or to other functional groups, including those which are metal-free, which can be used in cross-coupling reactions, and including —H. This Met group may more particularly be selected from one of the following functional groups:

—SnR*₃, —B(OR*)₂, —Zn-Hal*, —Mg-Hal*, where R* is a $C_1$-$C_{10}$ alkyl and where the group "Hal*" is a halogen, selected more particularly from the group containing: Cl, Br, I.

The building block Z of the general compound (I) containing M-N or N-M may therefore be prepared via C—C coupling reactions which are known to the skilled person:

or

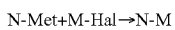

"Hal" here denotes a halogen substituent, more particularly selected from the group containing: Cl, Br, I. The starting compounds to be used for these reactions are either available commercially or can be obtained by typical metalation or halogenation reactions. The coupling to give the building block N-M or M-N may be carried out, for example, by Suzuki, Negishi or Stille, Kumada or Hiyama and further coupling reactions, which are described in sources including "Metal-Catalyzed Cross-Coupling Reactions, 2nd, Completely Revised and Enlarged Edition" (Wiley VCH, ISBN: 978-3-527-30518-6) (Suzuki: pages 41-123, Negishi: pages 619-670, Stille: pages 125-161, Kumada: pages 671-698, Hiyama: pages 163-216, further coupling reactions: pages 815-889). Generally, but not exclusively, the C—C cross-coupling reactions take place with use of a catalyst.

The introduction of further groups selected from N, M or T1 to T4 may be accomplished in turn by metalating one of the two components and halogenating or otherwise substituting the second coupling component, in order to effect activation suitably for C—C coupling reactions. In principle here it is possible to vary which coupling component is equipped with which activating group. Typically, in C—C coupling reactions, high reaction yields are achieved when the more electron-rich building block carries the "Met substituent" and the more electron-deficient building block carries the "Hal substituent". However, the inverse reaction regime may also lead to good results. The coupling of the further building blocks may then be carried out, again, by coupling reactions known to the skilled person, such as Suzuki, Negishi or Stille, Kumada or Hiyama coupling reactions, for example. The selection of a suitable coupling reaction is made by the skilled person with a view to the necessary reaction conditions and the compatibility thereof with any functional groups present. In these reactions, depending on the realization of the target compound, one or more building blocks per reaction step can be coupled to the scaffold.

Where one building block T is a component of the formula 11 or formula 11*, this building block may take place according to a customary route known to the skilled person for the introduction of double bonds. This route may involve, for example, Heck, Wittig and/or aldol reactions, or else eliminations, Cope or McMurry reactions, or the aforementioned C—C coupling reactions, which are described in sources including March's Advanced Organic Chemistry: Reactions, Mechanisms, and Structure, 7th Edition (ISBN: 978-0-470-46259-1) (chapter 12, pp. 649ff, chapter 13, pp. 732ff, chapter 16, pp. 1067ff, chapter 17, pp. 1253ff, chapter 19, pp. 1433ff.).

By the methods described it is possible to introduce any desired further building blocks from the group of N, M or T.

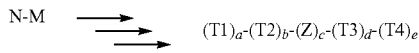

The electron-withdrawing groups EWG1 and EWG2 are generally introduced by an aldol condensation of a component of the formulae 7, 8 or 9, carrying an activated methylene unit, with a carbonyl component, which is introduced beforehand onto the adjacent moiety T, M or N by methods known to the skilled person such as, for example, Gattermann, Gattermann-Koch, Houben-Hoesch, Vilsmeier/Vilsmeier-Haack, Friedel-Crafts acylation or, following lithiation, by reaction with an acid derivative or carbonylation reagent, these being described in sources including Organikum (ISBN 978-3-527-33968-6—Wiley-VCH, chapters D2-D9).

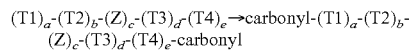

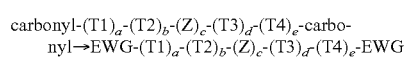

where the group "carbonyl" is the carbonyl component stated above. The sequence of the synthesis steps described can be varied arbitrarily. Hence it is possible, for example, to build up two molecular moieties of the general formula (I) by one of the methods described above, and to form the bond between the components M-N, N—N, M-M, N-T, M-T or T-T in the last reaction step.

Inventive compounds were synthesized by methods represented below, on the basis either of a. dual Stille coupling, b. dual inverse Stille coupling, or c. simple Stille coupling.

Set out below are the corresponding general operating protocols (GOP1 to GOP3) for versions a, b and c:

a) General Operating Protocol (GOP1)

1 mmol of distannyl compound reactant 1 and 2.5 mmol of reactant 2 were dissolved in 4 ml of corresponding solvent (table 4) and the solution was degassed. Then 0.05 mmol of Pd catalyst was added thereto and the reaction mixture was heated overnight. The reaction mixture was brought to room temperature, precipitate which formed in this operation was removed by filtration, and this precipitate was washed with methanol. The crude product was recrystallized from corresponding solvent.

TABLE 4

Reaction conditions for the synthesis of compounds 1, 2, 4, 5, 11

| Number | Reactant 1 | Reactant 2 | Reaction conditions | Yield (%) | Recrystallized from |
|---|---|---|---|---|---|
| 1 | A1 | B8 | $Pd(PPh_3)_4$/DMF/80° C. | 32 | Chlorobenzene |
| 2 | A1 | B6 | $Pd(PPh_3)_4$/DMF/80° C. | 34 | Chlorobenzene |
| 4 | A1 | B2 | $Pd(PPh_3)_4$/DMF/80° C. | 27 | Chlorobenzene |
| 5 | A2 | B2 | $Pd(PPh_3)_4$/1,4-dioxane/80° C. | 34 | Chlorobenzene |
| 11 | A1 | C14 | $Pd_2(dba)_3$/P(tert-Bu)$_3$/1,4-dioxane/80° C. | 43 | Chlorobenzene | b) General Operating Protocol (GOP2)

1 mmol of dibromo compound and 2.5 mmol of B4 were dissolved in 4 ml of dioxane and the solution was degassed. Then 0.05 mmol of Pd catalyst was added thereto and the reaction mixture was stirred at 80° C. overnight. The reaction mixture was brought to room temperature, precipitate formed was removed by filtration, and this precipitate was washed with methanol.

TABLE 5

Reaction conditions for the synthesis of compound 6 and 12

| Number | Reactant 1 | Reactant 2 | Reaction conditions | Yield (%) | Recrystallized from |
|---|---|---|---|---|---|
| 6 | A3 | B4 | $Pd_2dba_3$/P(t-Bu)$_3$•$HBF_4$/80° C. | 40 | Chlorobenzene |
| 12 | A8 | B4 | $Pd_2dba_3$/P(t-Bu)$_3$/dioxane/60° C. | 13 | Tetrahydrofuran/hexane | c) General Operating Protocol (GOP3)

In a Schlenk vessel rendered inert using argon, 1 mmol of halogen compound reactant 1 and 1.2 mmol of 2-[3-(5-trimethylstannanylfuran-2-yl)allylidene]malononitrile B4 reactant 2 were dissolved in 3 ml of solvent. The solution was degassed, then 0.05 mmol of Pd catalyst was added and the reaction mixture was heated overnight with stirring. The reaction mixture was cooled to room temperature, the resulting precipitate was removed by filtration, and this precipitate was washed with methanol. The crude product was recrystallized from the respective solvent (table 5).

TABLE 6

Reaction conditions for the synthesis of compounds 3, 7, 8, 9, 10, 13 to 17

| Number | Reactant 1 | Reactant 2 | Reaction conditions | Yield/% | Recrystallized from |
|---|---|---|---|---|---|
| 3 | C4 | B4 | Pd2(dba)3/P(tBu)3, 1,4-dioxane, 80° C. | 72 | Tetrahydrofuran/hexane |
| 7 | C6 | B4 | Pd2(dba)3/P(tBu)3, 1,4-dioxane, 80° C. | 62 | Tetrahydrofuran |
| 8 | C10 | B4 | Pd2(dba)3/P(tBu)3, 1,4-dioxane, 80° C. | 26 | Tetrahydrofuran/hexane |
| 9 | C2 | B4 | $Pd(PPh_3)_4$, tetrahydrofuran, 65° C. | 9 | Tetrahydrofuran/hexane |
| 10 | C8 | B4 | Pd2(dba)3/P(tBu)3, 1,4-dioxane, 80° C. | 48 | Tetrahydrofuran/hexane |
| 13 | C25 | B4 | Pd2(dba)3/P(tBu)3, 1,4-dioxane, 80° C. | 20 | Purified by column chromatography (dichloromethane) |
| 14 | C27 | B4 | Pd(PtBu3)2 1,4-dioxane, 80° C. | 39 | Toluene |
| 15 | C37 | B4 | Pd(PtBu3)2 1,4-dioxane, 60° C. | 59 | Toluene |
| 16 | C23 | B4 | Pd(PtBu3)2, 1,4-dioxane, 60° C. | 55 | Chlorobenzene |
| 17 | C39 | B4 | Pd(PtBu3)2, 1,4-dioxane, 60° C. | 80 | Tetrahydrofuran/hexane |

Alternatively it is also possible for inventive compounds to take place via other known C—C coupling reactions such as, for example, Suzuki or Neghishi reaction.

The reactants 1 (A), reactants 2 (B) and reactants 3 (C) may be synthesized according to the following protocols:

Synthesis of Compounds A1-A19

N-Propyl-2,5-bis-trimethylstannyl-pyrrole (A1)

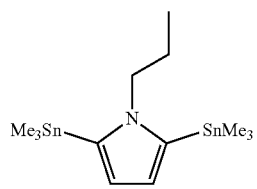

A1

The compound was prepared in accordance with the literature reference of G. H. Jana et al. Bioorg. Med. Chem. Lett., 2015, (15), 3592-3595. Instead of tributyltin chloride, trimethyltin chloride was used.

The crude product was recrystallized from methanol to give product A1 in 35% yield as a colorless solid. $^1$H-NMR (CDCl$_3$): 6.40 ppm (s, 2H), 3.88 (m, 2H), 1.76 (m, 2H), 0.97 (t, 3H), 0.32 (s, 18H).

N-Methyl-2,5-bis-trimethylstannyl-pyrrole (A2)

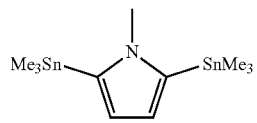

A2

The compound was prepared in accordance with the literature reference of G. H. Jana et al. Bioorg. Med. Chem. Lett., 2015, (15), 3592-3595. Instead of tributyltin chloride, trimethyltin chloride was used.

The crude produce was recrystallized from isopropanol to give product A2 in 34% yield as a colorless solid. $^1$H-NMR (CDCl$_3$): 6.39 ppm (s, 2H), 3.75 (s, 3H), 0.32 (s, 18H).

2,5-Dibromo-1-ethyl-pyrrole (A3)

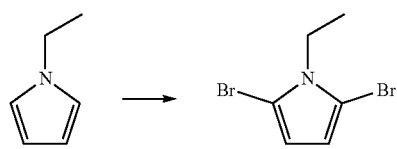

A3

951 mg (10.0 mmol) of 1-ethylpyrrole were dissolved in 50 ml of THF at −78° C. under an argon atmosphere. 3.60 g (20.0 mmol) of NBS were added over the course of 15 minutes. The reaction mixture was stirred at −78° C. for 4 hours and then warmed to RT overnight. The reaction mixture was admixed with 100 ml of saturated Na$_2$SO$_3$ solution and extracted twice with MTBE. The combined organic phases were washed with saturated NaCl solution. They were dried over Na$_2$SO$_4$ and filtered and the solvents were removed under reduced pressure. The residue was purified by chromatography on silica gel to 1.00 g of product A3 (40%) as a colorless oil. GC-MS (EI, 75 eV) m/z 252.9 (M$^+$, 100%).

1-Methyl-2-trimethylstannanyl-1H-pyrrole (A4)

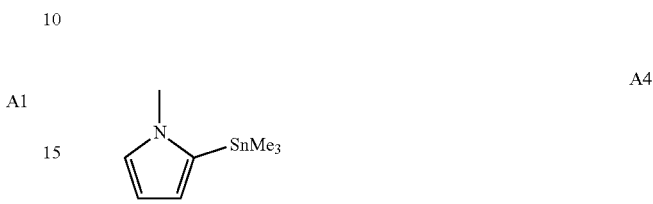

A4

The synthesis took place in analogy to Groenendaal et al. Synth. Commun. 1995, 25 (10), 1589-1600

1-Propyl-2-trimethylstannanyl-1H-pyrrole (A5)

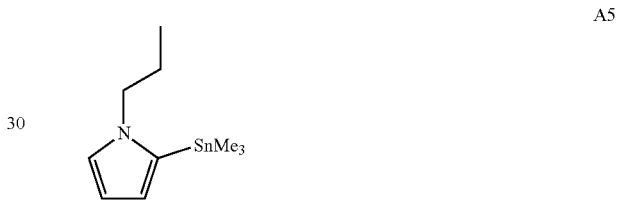

A5

The synthesis took place in analogy to Groenendaal et al. Synth. Commun. 1995, 25 (10), 1589-1600

1-Ethyl-2-trimethylstannanyl-1H-pyrrole (A6)

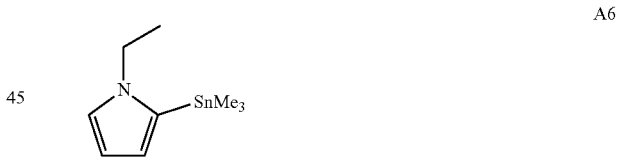

A6

The synthesis took place in analogy to Groenendaal et al. Synth. Commun. 1995, 25 (10), 1589-1600

1-Phenyl-2-trimethylstannanyl-1H-pyrrole (A7)

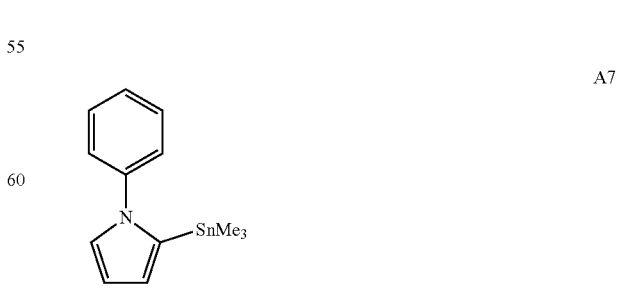

A7

The synthesis took place in analogy to Groenendaal et al. Synth. Commun. 1995, 25 (10), 1589-1600

2,5-Dibromo-1-phenyl-pyrrole (A8)

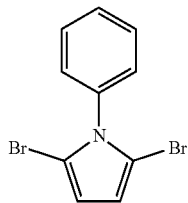

1446 mg (10.0 mmol) of 1-phenylpyrrole were dissolved in 50 ml of THF at −78° C. under an argon atmosphere. 3.60 g (20.0 mmol) of NBS were added over the course of 15 minutes. The reaction mixture was stirred at −78° C. for 4 hours and then warmed to RT overnight. The reaction mixture was admixed with 100 ml of saturated $Na_2SO_3$ solution and extracted twice with MTBE. The combined organic phases were washed with saturated NaCl solution. They were dried over $Na_2SO_4$ and filtered and the solvents were removed under reduced pressure. The residue was purified by chromatography on silica gel to 2.75 g of product A8 (91%) as a colorless solid. $^1$H-NMR (acetone-d6): 7.57 ppm (m, 3H), 7.31 (dd, 2H), 6.38 (s, 1H).

General Protocol for the Synthesis of Pyrroles from Dimethoxytetrahydrofuran

The syntheses take place in analogy to literature protocol from Sunil Kumar et al., J. Phys. Chem. C, 2014, 118 (5), 2570:

50 mmol of sodium acetate were dissolved in 100 ml of demineralized water at room temperature, and 50 mmol of the corresponding amine were added. 25 ml of glacial acetic acid were slowly added dropwise thereto and the mixture was heated to 80° C. 50 mmol of 2,5-dimethoxytetrahydrofuran were added dropwise and the reaction mixture was stirred at 80° C. for 16 hours. The reaction solution was then brought to room temperature and extracted with dichloromethane. The organic phase was washed with saturated NaCl solution, dried over sodium sulfate and concentrated on a rotary evaporator. The crude product was purified by chromatography.

| Structure | Number | Yield | Characterization |
|---|---|---|---|
| 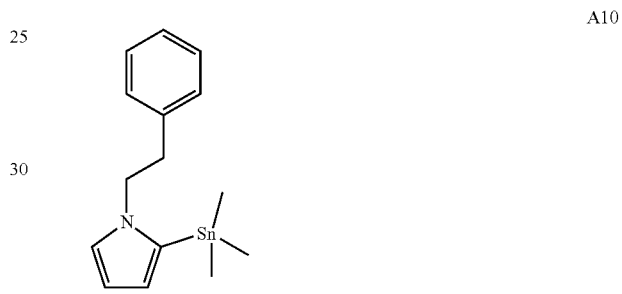 | A13 | 82 | GC-MS m/z: 177 [M] |
| 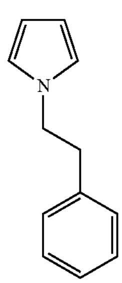 [SMILES: c1ccc(CCn2cccc2)cc1] | A9 | 96 | GC-MS m/z: 171 [M], 104, 80 |
| | A16 | 80 | GC-MS m/z: 132 [M] |

Synthesis of 1-phenethyl-2-trimethylstannyl-1H-pyrrole (A10)

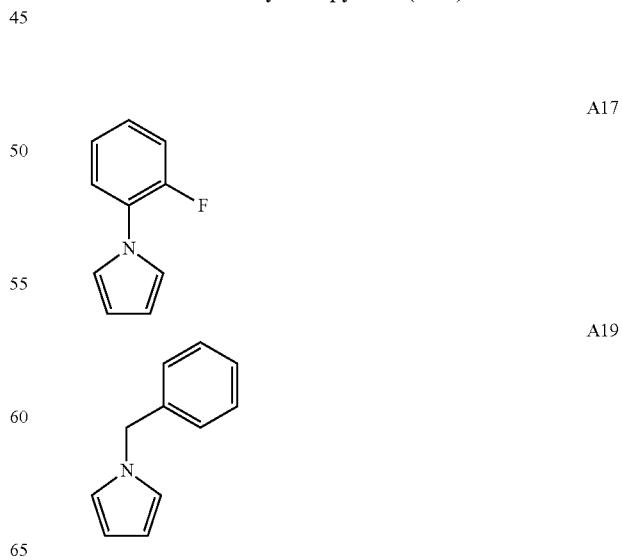

The synthesis of A10 took place in analogy to Groenendaal et al. Synth. Commun. 1995, 25 (10), 1589-1600

1-(2-Fluoro-phenyl)-1H-pyrrole (A17)

1-Benzyl-1H-pyrrole (A19)

The compounds A17 and A19 are available commercially.

Synthesis of the Compounds B1-B8

(E)-3-(5-Bromo-furan-2-yl)-propenal (B1)

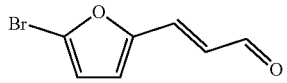

The synthesis of B1 takes place according to the literature reference of I. I. Popov, Z. N. Nazarova, A. P. Chumak, Chem. Heterocycl. Compd., 1978, 14, (3), 253-255:

50 mmol of 5-bromo-2-furfural were suspended in 100 ml of 6% NaOH solution. Acetaldehyde in 15 ml of water was added dropwise to the reaction mixture at 0° C. Stirring was continued at 0° C. for 1 hour. The precipitate was isolated by filtration, washed with water and dried. The crude product was purified by chromatography on silica gel. Yield 74%. 1H-NMR (acetone-d6): 9.64 ppm (d, 1H), 7.44 (d, 1H), 7.04 (d, 1H), 6.73 (d, 1H), 6.47 (dd, 1H).

(E)-3-(5-Bromo-furan-2-yl)-allylidene]-malononitrile (B2)

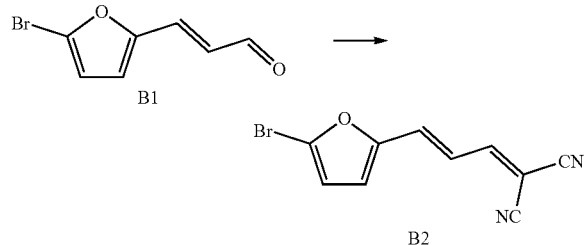

36.7 mmol of (E)-3-(5-bromo-furan-2-yl)-propenal and 44.0 mmol of malononitrile were dissolved in 50 ml of ethanol. 3.7 mmol of f-alanine were added thereto and the reaction mixture was stirred at room temperature for 24 hours. The precipitate formed was briefly heated to boiling and then cooled in an ice bath. The solid which crystallized out was isolated by filtration and washed with a little ethanol. Drying in a desiccator led to the isolation of 3.49 g of [(E)-3-(5-bromo-furan-2-yl)-allylidene]-malononitrile B2 (38% yield). EI m/z: 250[M], 169, 141, 114.

(E)-3-(5-Trimethylstannyl-furan-2-yl)-propenal (B3)

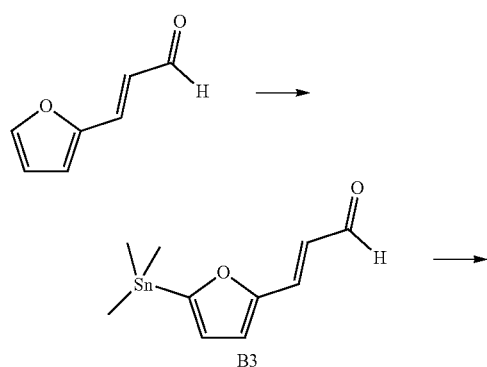

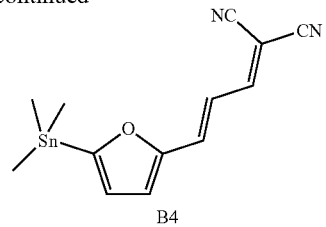

A solution of 3.06 g (29.9 mmol) of 1-methylpiperazine in 82 ml of anhydrous THF was admixed dropwise under an argon atmosphere and at −78° C. with 12 ml (30 mmol) of n-butyllithium solution (2.5M in hexane). After 15 minutes of stirring, 3.15 g (25.0 mmol) of trans-3-(2-furyl)acrolein were added dropwise. After a further 15 minutes of stirring, 3.95 g (33.7 mmol) of N,N,N',N'-tetramethylethylenediamine were added dropwise. After 15 minutes of stirring, 13.4 ml (33.5 mmol) of n-butyllithium solution (2.5M in hexane) were added dropwise. The reaction mixture was stirred at −20° C. for 3 hours and then cooled again to −78° C. At this temperature, 29.9 ml (29.9 mmol) of a 1M solution of trimethyltin chloride in THF were added and the mixture was subsequently stirred at R.T. for 16 hours. Then 100 ml of water were added, the organic phase was removed, the aqueous phase was extracted three times with MTBE, and the combined organic phases were washed with 80 ml each of 1M hydrochloric acid, saturated ammonium chloride solution and brine. After drying over sodium sulfate, the solvents were removed by distillation and the residue was purified by chromatography (SiO2, petroleum ether/MTBE 5/1). Yield 5.52 g (76%). 1H-NMR (400 MHz) in acetone-d6: 0.38 (s, 9H), 6.48 (dd, 1H), 6.84 (d, 1H), 6.97 (d, 1H), 7.51 (d, 1H), 9.63 (d, 1H).

2-[(E)-3-(5-Trimethylstannanyl-furan-2-yl)-allylidene]-malononitrile (B4)

Under an argon atmosphere, 9.52 g (33.4 mmol) of B3 and 2.23 g (33.4 mmol) of malodinitrile were dissolved in 19 ml of ethanol. 152 mg (1.67 mmol) of beta-alanine were added and the mixture was stirred at R.T. for 4 hours. It was then heated to reflux temperature and cooled slowly to 0° C. with stirring. The precipitate was isolated by filtration, washed with 2 ml of ethanol and dried under reduced pressure: 9.10 g (82%) of orange crystalline solid. 1H-NMR (400 MHz) in acetone-d6: 0.41 (s, 9H), 6.90 (d, 1H), 7.07 (m, 2H), 7.46 (d, 1H), 8.01 (d, 1H).

3-(5-Bromo-furan-2-yl)-cyclohex-2-enone (B5)

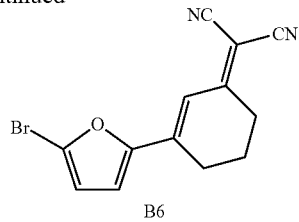

B6

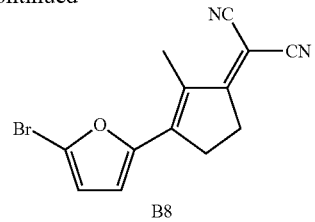

B8

Under an argon atmosphere, a solution of 2.00 g of 2,5-dibromofuran (8.85 mmol) in 25 ml of diethyl ether was admixed dropwise at −65° C. and with stirring with 5.53 ml of n-butyllithium (1.6M in hexane) over the course of 15 minutes. After a further 15 minutes, 1.86 g of 3-ethoxy-2-cyclohexen-1-one (13.3 mmol) were added and the mixture was heated overnight at R.T. The mixture was added to 150 ml of brine and extracted with 3×100 ml of dichloromethane. The combined organic extracts were washed with 2M hydrochloric acid and dried over sodium sulfate and the solvents were removed under reduced pressure. Purification by column chromatography (SiO$_2$, dichloromethane) gave B5 as a yellow crystalline solid (1.08 g, 4.48 mmol, 51%). $^1$H-NMR (CDCl$_3$): 6.68 ppm (d, 1H), 6.44-6.43 (m, 2H), 2.60 (td, 2H), 2.46 (t, 2H), 2.14-2.07 (m, 2H).

2-[3-(5-Bromo-furan-2-yl)-cyclohex-2-enylidene]-malononitrile (B6)

Under an argon atmosphere, 1.68 g of ammonium acetate (21.8 mmol) were added to a solution of 1.74 g of B5 (7.14 mmol) and 1.42 g of malononitrile (21.5 mmol) in dichloroethane. The mixture was refluxed for 2 hours, then 20 mg of 1,4-diazabicyclo[2.2.2]octane (0.178 mmol) were added, followed by refluxing for a further 16 hours. The reaction mixture was added to 100 ml of water and extracted with 3×50 ml of dichloromethane. The combined organic extracts were washed with 100 ml of water and dried over sodium sulfate and the solvents were removed under reduced pressure. Purification by column chromatography (SiO$_2$, hexane) gave B6 as an orange crystalline solid (1.15 g, 3.98 mmol, 91%). $^1$H-NMR (CDCl$_3$): 7.19 ppm (s, 1H), 6.79 (d, 1H), 6.49 (d, 1H), 2.80 (t, 2H), 2.64-2.61 (m, 2H), 2.00-1.94 (m, 2H).

3-(5-Bromo-furan-2-yl)-2-methyl-cyclopent-2-enone (B7)

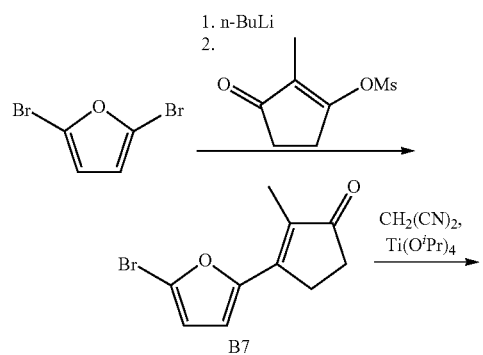

Under an argon atmosphere, a solution of 3.46 g of 2,5-dibromofuran (15 mmol) in 45 ml of diethyl ether was admixed dropwise at −65° C. and with stirring with 6.00 ml of n-butyllithium (2.5M in hexane, 15 mmol) over the course of 30 minutes. After a further 15 minutes, 2.94 g of 3-ethoxy-2-methyl-2-cyclopenten-1-one (21.0 mmol) in solution in 15 ml of diethyl ether were added and the mixture was stirred at −65° C. for 1.5 hours and then warmed to R.T. overnight. Following the addition of 150 ml of dichloromethane, the mixture was added to 300 ml of 1M hydrochloric acid. The organic phase was removed and the aqueous phase was extracted once with 100 ml of dichloromethane. The combined organic phases were washed with 2M hydrochloric acid (150 ml) and water (100 ml) and dried over sodium sulfate and the solvents were removed under reduced pressure. Purification by column chromatography (SiO$_2$, dichloromethane/hexane) gave B7 as a yellow crystalline solid (2.10 g, 8.71 mmol, 58%). $^1$H-NMR (CDCl$_3$): 6.75 ppm (d, 1H), 6.50 (d, 1H), 2.86-2.82 (m, 2H), 2.52-2.49 (m, 2H), 2.02 (t, 3H).

2-[3-(5-Bromo-furan-2-yl)-2-methyl-cyclopent-2-enylidene]-malononitrile (B8)

A solution of 1.30 g of 3-(5-bromofuran-2-yl)-2-methyl-cyclopent-2-enone (5.39 mmol) and 3.60 g of malononitrile (53.9 mmol) in 1,2-dichloroethane was admixed under an argon atmosphere with 3.09 g of tetraisopropyl orthotitanate (10.8 mmol) and stirred under reflux for 3 days. The reaction mixture was poured onto hydrochloric acid (1M, 200 ml), stirred vigorously for 30 minutes and extracted with dichloromethane (3×100 ml). The combined organic phases were washed with water (100 ml), dried over sodium sulfate and filtered, and the solvent was removed under reduced pressure. Purification by column chromatography (silica gel, dichloromethane) gave B8 (1.37 mg, 4.75 mmol, 88%) as an orange-colored crystalline solid. $^1$H-NMR (CDCl$_3$): 6.82 ppm (d, 1H), 6.55 (d, 1H), 3.09-3.06 (m, 2H), 3.00-2.96 (m, 2H), 2.40 (t, 3H).

Synthesis of the Compounds C1-C39

2-[5-(1-Methyl-1H-pyrrol-2-yl)-furan-2-ylmethylene]-malononitrile (C1)

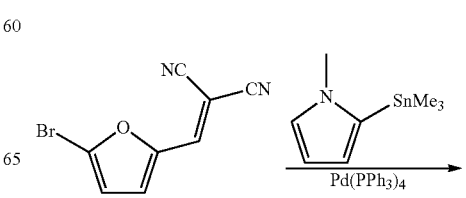

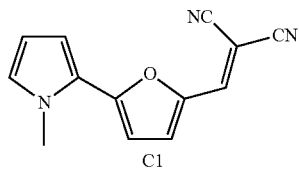

In a baked Schlenk vessel, C12 (1.01 g, 4.52 mmol) and A4 (849 mg, 3.48 mmol) were introduced under argon in dry tetrahydrofuran (5 ml), and tetrakis-(triphenylphosphine)-palladium(0) (101 mg, 87 µmol) was added. The reaction mixture was stirred at a bath temperature of 80° C. for 16 hours, poured onto water (about 150 ml) and extracted with dichloromethane (3×100 ml). The combined organic phases were dried over sodium sulfate and filtered and the solvent was removed under reduced pressure. Purification by column chromatography (silica gel, dichloromethane/petroleum ether) afforded C1 (420 mg, 1.88 mmol, 54%) as a red crystalline solid. $^1$H-NMR (acetone-$D_6$): 7.84 ppm (s, 1H), 7.52 (d, 1H), 7.03-7.02 (m, 1H), 6.97 (d, 1H), 6.90 (dd, 1H), 6.21 (dd, 1H), 4.00 (s, 3H).

2-[5-(1-Propyl-1H-pyrrol-2-yl)-furan-2-ylmethylene]-malononitrile (C3)

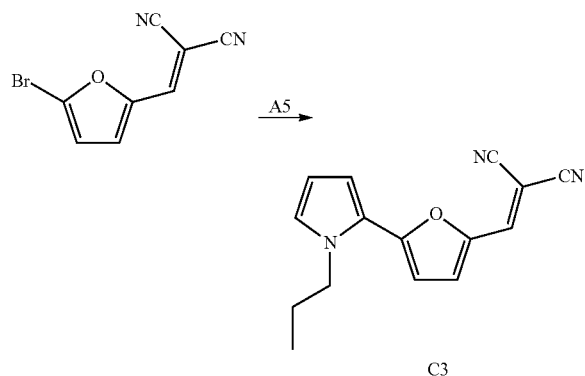

In a baked Schlenk vessel, C12 (669 mg, 3.00 mmol) and A5 (1.10 g, 3.00 mmol) were introduced under argon in dry tetrahydrofuran (5 ml), and tetrakis-(triphenylphosphine)-palladium(0) (87 mg, 75 µmol) was added. The reaction mixture was stirred at a bath temperature of 70° C. for 16 hours, poured onto about 150 ml of water and extracted with dichloromethane (3×100 ml). The combined organic phases were dried over sodium sulfate and filtered and the solvent was removed under reduced pressure. Purification by column chromatography (silica gel, dichloromethane/petroleum ether) afforded C3 (500 mg, 1.99 mmol, 66%) as an orange-colored viscous oil. $^1$H-NMR (acetone-$d_6$): 7.85 ppm (s, 1H), 7.53 (d, 1H), 7.10 (dd, 1H), 6.95-6.93 (m, 2H), 6.23 (dd, 1H), 4.36 (t, 2H), 1.75 (sext, 2H), 0.88 (t, 3H).

2-[5-(1-Methyl-1H-pyrrol-2-yl)-thiophen-2-ylmethylene]-malononitrile (C5)

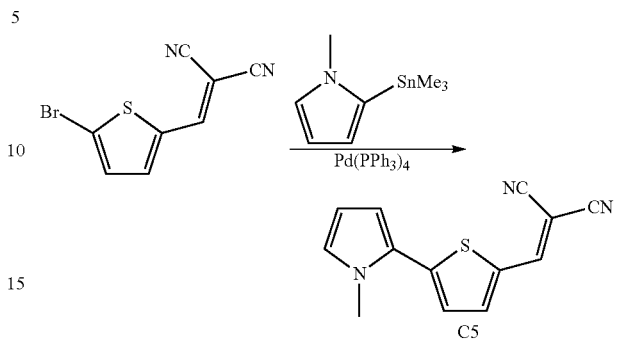

In a baked Schlenk vessel, C11 (1.09 g, 4.55 mmol) and A4 were introduced under argon in dry tetrahydrofuran (7 ml), and tetrakis-(triphenylphosphine)-palladium(0) (105 mg, 91 µmol) was added. The reaction mixture was stirred at a bath temperature of 80° C. for 16 hours, poured onto water (about 150 ml) and extracted with dichloromethane (3×100 ml). The combined organic phases were dried over sodium sulfate and filtered and the solvent was removed under reduced pressure. Purification by column chromatography (silica gel, dichloromethane/petroleum ether) afforded C5 (670 mg, 2.80 mmol, 80%) as a red crystalline solid. $^1$H-NMR (CDCl$_3$): 7.74 ppm (s, 1H), 7.66 (d, 1H), 7.19 (d, 1H), 6.84-6.82 (m, 1H), 6.68 (dd, 1H), 6.23 (dd, 1H), 3.87 (s, 3H).

2-[5-(1-Ethyl-1H-pyrrol-2-yl)-thiophen-2-ylmethylene]-malononitrile (C7)

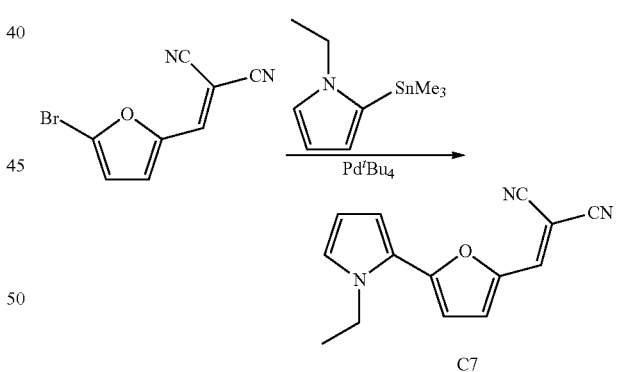

In a baked Schlenk vessel, C12 (989 mg, 4.43 mmol) and A6 (1.10 g, 3.41 mmol) were introduced under argon in dry dioxane (5 ml) and degassed for 10 minutes, and tris-(dibenzylideneacetone)-dipalladium(0) (81 mg, 85 µmol) and tri-tert-butylphosphine tetrafluoroborate (100 mg, 341 µmol) were added. The reaction mixture was stirred at a bath temperature of 80° C. for 16 hours, poured onto water (about 150 ml) and extracted with dichloromethane (3×100 ml). The combined organic phases were dried over sodium sulfate and filtered and the solvent was removed under reduced pressure. Purification by column chromatography (silica gel, dichloromethane) afforded C7 (820 mg, 3.46 mmol, 78%) as a red solid. $^1$H-NMR (acetone-$D_6$): 7.85 ppm (s, 1H), 7.54 (d, 1H), 7.12-7.11 (m, 1H), 6.98 (d, 1H), 6.94-6.93 (m, 1H), 6.25-6.23 (m, 1H), 4.43 (q, 2H), 1.39 (t, 3H).

2-[5-(1-Phenyl-1H-pyrrol-2-yl)-furan-2-ylmethylene]-malononitrile (C9)

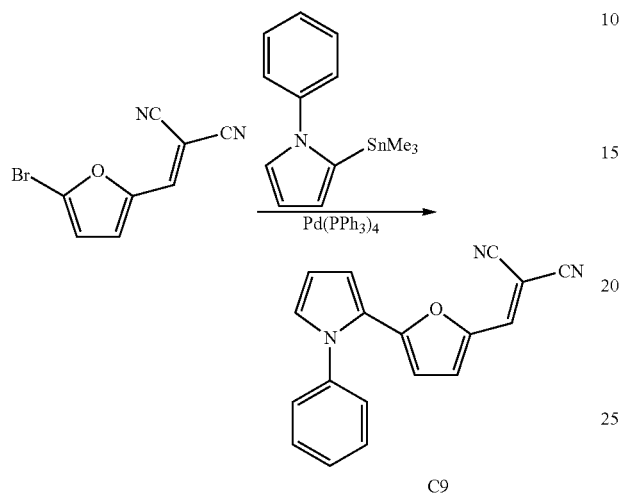

C9

In a baked Schlenk vessel, C12 (1.45 g, 6.50 mmol) and A7 (1.91 mg, 5.00 mmol) were introduced in dry 1,4-dioxane (7.5 ml) under argon. Tri-tert-butylphosphine tetrafluoroborate (147 mg, 0.50 mmol) and tris-(dibenzylideneacetone)-dipalladium(0) (118 mg, 125 μmol) are added. The reaction mixture was stirred at a bath temperature of 80° C. for 16 hours, poured onto water (about 150 ml) and extracted with dichloromethane (3×100 ml). The combined organic phases were dried over sodium sulfate and filtered and the solvent was removed under reduced pressure. Purification by column chromatography (silica gel, dichloromethane/petroleum ether) gave 2-[5-(1-phenyl-1H-pyrrol-2-yl)-furan-2-ylmethylene]malononitrile (1.35 g, 4.73 mmol, 94%) as a red crystalline solid.

1H-NMR (acetone-$D_6$): 7.82 ppm (s, 1H), 7.59 (m, 3H), 7.47 (m, 2H), 7.28 (d, 1H), 7.17 (m, 1H), 7.07 (m, 1H), 6.47 (m, 1H), 5.57 (d, 1H).

2-(5-Bromo-thiophen-2-ylmethylene)-malononitrile (C11)

2-(5-Bromo-furan-2-ylmethylene)-malononitrile (C12)

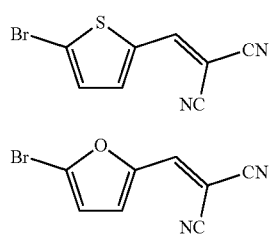

Compounds C11 and C12 are prepared in accordance with the literature-described synthesis (Qi et al., J. Mat. Chem. 2008, 18, 1131).

2-(5-Furan-2-yl-thiophen-2-ylmethylene)-malononitrile (C13)

2-[5-(5-Bromo-furan-2-yl)-thiophen-2-ylmethylene]-malononitrile (C14)

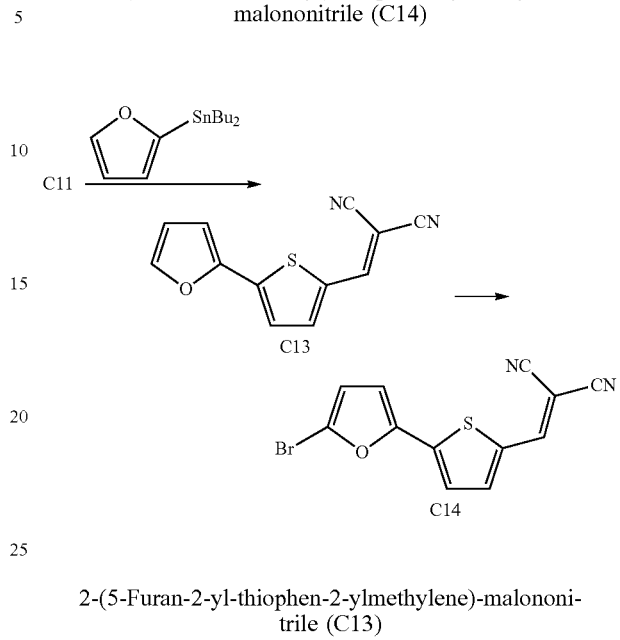

2-(5-Furan-2-yl-thiophen-2-ylmethylene)-malononitrile (C13)

In a baked Schlenk vessel, C11 (2.39 g, 10.0 mmol) and 2-tributylstannylfuran (4.79 g, 13.0 mmol) in dry 1,4-dioxane (14.9 ml) were introduced under argon. Tri-tert-butylphosphine tetrafluoroborate (293 mg, 1.00 mmol) and tris-(dibenzylideneacetone)-dipalladium(0) (236 mg, 250 μmol) are added. The reaction mixture was stirred at a bath temperature of 80° C. for 16 hours. The orange suspension was filtered and the residue was recrystallized from ethanol. This gave product C13 (1.67 g, 4.73 mmol, 74%) as an orange crystalline solid.

$^1$H-NMR (CDCl$_3$): 7.78 ppm (s, 1H), 7.67 (d, 1H), 7.55 (d, 1H), 7.36 (d, 1H), 6.85 (d, 1H), 6.56 (dd, 1H).

2-[5-(5-Bromo-furan-2-yl)-thiophen-2-ylmethylene]-malononitrile (C14)

2-(5-Furan-2-yl-thiophen-2-ylmethylene)-malononitrile (C13) (1.11 g, 4.86 mmol) was introduced under argon in dry tetrahydrofuran (44 ml) at −70° C., and N-bromosuccinimide (874 mg, 4.86 mmol) was added. The reaction mixture was stirred at −70° C. in the absence of light for 30 minutes and was gradually warmed to room temperature overnight in a cold bath. Following the addition of 50 ml of water, the product was isolated by filtration and dried. The residue was recrystallized from ethanol to give the product C14 (1200 mg, 3.93 mmol, 81%) as an orange crystalline solid.

$^1$H-NMR (CDCl$_3$): 7.78 ppm (s, 1H), 7.66 (d, 1H), 7.35 (d, 1H), 6.79 (d, 1H), 6.49 (d, 1H).

General Protocol for Bromination and Stille Coupling 1 mmol of the corresponding pyrrole was dissolved in 25 ml of dry THF and cooled to −78° C. under argon. 0.8 mmol of NBS, in solution in 10 ml of dry THF, was slowly added dropwise at −78° C. and the reaction mixture was stirred at −78° C. for 2 hours. The mixture was subsequently brought to room temperature and 35 ml of dioxane, 1.2 mmol of 2-(5-trimethylstannanyl-furan-2-ylmethylene)-malononitrile (C18) and 1 mol % of Pd[P(t-Bu3)]2 were added. The reaction mixture was stirred at 80° C. for 16 hours. Purification by column chromatography (silica gel, dichloromethane) afforded the corresponding product.

| Structure | Number | Reactant | Yield | Characterization |
|---|---|---|---|---|
| [structure: 1-(4,4,4-trifluorobutyl)pyrrole-furan-dicyanovinyl] | C26 | A13 | 58% | GC-MS m/z: 319 [M], 222, 180, 104, 77 |
| [structure: 1-(2-phenylethyl)pyrrole-furan-dicyanovinyl] | C24 | A10 | 55% | ¹H-NMR (CDCl3) ppm: 7.28 (s, 1H), 7.20 (m, 5H), 6.96 (d, 2H), 6.82 (d, 1H), 6.62 (d, 2H), 6.18 (d, 1H), 4.60 (t, 2H), 3.03 (t, 2H). |
| [structure: 1-(p-tolyl)pyrrole-furan-dicyanovinyl] | C22 | A16 | 32% | 1H-NMR (acetone-d6): 7.82 ppm (s, 1H), 7.41 (m, 2H), 7.34 (m, 2H), 7.25 (d, 1H), 7.13 (m, 1H), 7.05 (m, 1H), 6.45 (m, 1H), 5.57 (d, 1H), 2.46 (s, 3H). |
| [structure: 1-(2-fluorophenyl)pyrrole-furan-dicyanovinyl] | C36 | A17 | 40% | ¹H-NMR (DMSO-d6): 8.08 ppm (s, 1H), 7.59-7.66 (m, 2H), 7.52 (t, 1H), 7.42 (t, 1H), 7.31 (m, 2H), 6.96 (m, 1H), 6.52 (m, 1H), 5.58 (d, 1H). |
| [structure: 1-benzylpyrrole-furan-dicyanovinyl] | C38 | A19 | 25% | 1H-NMR (acetone-d6): 7.82 ppm (s, 1H), 7.41 (m, 1H), 7.30 (m, 2H), 7.23 (m, 2H), 7.06 (m, 2H), 6.99 (d, 1H), 6.76 (d, 1H), 6.34 (d, 1H), 5.65 (s, 2H). |

General Protocol for Bromination 1 mmol of reactant 1 was introduced under argon in dry tetrahydrofuran (10 ml) at −70° C., and N-bromosuccinimide (178 mg, 1 mmol) was added. The reaction mixture was stirred in the absence of light and gradually warmed to room temperature overnight in a cold bath. Following the addition of triethylamine (1 ml), the solvent was removed under reduced pressure. Purification by column chromatography (silica gel, dichloromethane) afforded the corresponding brominated product.

| Product | Reactant 1 | | Yield/% | Analysis |
|---|---|---|---|---|
| C4 | NC-C(CN)=CH-[5-(1-propyl-pyrrol-2-yl)furan-2-yl] | C3 | 68 | ¹H-NMR (CDCl₃): 7.31-7.28 ppm (m, 2H), 6.83 (d, 1H), 6.64 (d, 1H), 6.31 (d, 1H), 4.34 (t, 2H), 1.73 (sext, 2H), 0.92 (t, 3H). |
| C6 | NC-C(CN)=CH-[5-(1-methyl-pyrrol-2-yl)thiophen-2-yl] | C5 | 78 | ¹H-NMR (CDCl₃): 7.75 ppm (s, 1H), 7.68 (d, 1H), 7.16 (d, 1H), 6.61 (d, 1H), 6.31 (d, 1H), 3.81 (s, 3H). |
| C10 | NC-C(CN)=CH-[5-(1-phenyl-pyrrol-2-yl)furan-2-yl] | C9 | 37 | ¹H-NMR (acetone-D₆): 7.84 ppm (s, 1H), 7.68-7.70 (m, 3H), 6.46 (m, 2H), 7.23 (d, 1H), 7.04 (d, 1H), 6.60 (d, 1H), 5.27 (d, 1H). |
| C2 | NC-C(CN)=CH-[5-(1-methyl-pyrrol-2-yl)furan-2-yl] | C1 | 93 | ¹H-NMR (CDCl₃): 7.30 ppm (s, 1H), 7.26-7.25 (m, 1H), 6.79 (d, 1H), 6.68 (d, 1H), 6.32 (d, 1H), 3.94 (s, 3H). |
| C8 | NC-C(CN)=CH-[5-(1-ethyl-pyrrol-2-yl)furan-2-yl] | C7 | 50 | ¹H-NMR (acetone-D₆): 7.91 ppm (s, 1H), 7.56 (d, 1H), 7.05 (d, 1H), 6.98 (d, 1H), 6.41 (d, 1H), 4.49 (q, 2H), 1.33 (t, 3H). |
| C25 | NC-C(CN)=CH-[5-(1-(2-phenylethyl)-pyrrol-2-yl)furan-2-yl] | C24 | 94 | ¹H-NMR (CDCl3) ppm: 7.93 (s, 1H), 7.57 (d, 1H), 7.08 (d, 1H), 6.99 (d, 1H), 6.44 (d, 1H), 4.59 (t, 2H), 2.35 (m, 2H), 1.99 (m, 2H). |
| C27 | NC-C(CN)=CH-[5-(1-(4,4,4-trifluorobutyl)-pyrrol-2-yl)furan-2-yl] | C26 | 95 | ¹H-NMR (acetone-D₆) ppm: 7.28 (s, 1H), 7.17 (m, 4H), 6.96 (d, 2H), 6.74 (d, 1H), 6.49 (d, 1H), 6.32 (d, 1H), 4.64 (t, 2H), 2.97 (m, 2H). |

-continued

| Product | Reactant 1 | | Yield/% | Analysis |
|---|---|---|---|---|
| C37 | [structure: NC-C(CN)=CH-furan-pyrrole-N-(2-fluorophenyl)] | C36 | 80 | 1-HNMR (acetone-D6): 7.86 ppm (s, 1H), 7.75-7.81 (m, 1H), 7.63 (m, 1H), 7.53 (m, 2H), 7.28 (d, 1H), 7.08 (d, 1H), 6.67 (d, 1H), 5.47 (d, 1H). |
| C23 | [structure: NC-C(CN)=CH-furan-pyrrole-N-(4-methylphenyl)] | C22 | 79 | 1H-NMR (DMSO-D6): 8.09 ppm (s, 1H), 7.45 (d, 2H), 7.34 (d, 2H), 7.25 (d, 1H), 6.89 (d, 1H), 6.66 (d, 1H), 5.20 (d, 1H), 2.45 (s, 3H). |
| C39 | [structure: NC-C(CN)=CH-furan-pyrrole-N-benzyl] | C38 | 74 | 1H-NMR (DMSO-D6): 7.99 ppm (s, 1H), 7.44 (d, 1H), 7.31 (m, 2H), 7.24 (m, 1H), 6.98 (m, 3H), 6.84 (d, 1H), 6.55 (d, 1H), 5.62 (s, 2H). |

The invention is not confined by the description with reference to the working examples. The invention instead embraces every new feature and also every combination of features, including in particular every combination of features in the claims, even if that feature or that combination itself is not given explicitly in the claims or working examples.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A compound of formula I:

$$\text{EWG1-(T1)}_a\text{-(T2)}_b\text{-(Z)}_c\text{-(T3)}_d\text{-(T4)}_e\text{-EWG2},$$

wherein parameters a, b, d and e are each independently of one another 0 or 1, wherein parameter c is 1, 2, 3, 4 or 5, wherein group Z is a block of two groups M and N, linked as *-M-N—* or *—N-M-*, where * designates the attachment to the groups T1 to T4 or electron-withdrawing groups EWG1 and EWG2, wherein the group M each independently of one another are selected from:

Formula 1

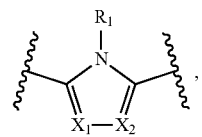

-continued

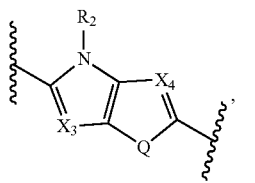

Formula 2

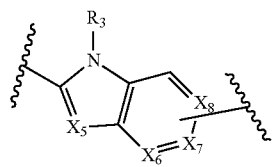

Formula 3 wherein the group N each independently of one another are selected from:

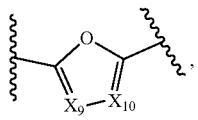

Formula 4

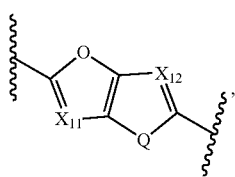

Formula 5

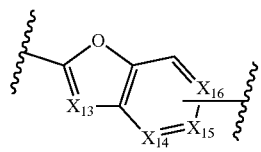

Formula 6 wherein the group M and the group N are each linked such that at least one N atom of the group M and one O atom of the group N are each joined to one another via 2 C atoms, and $\ell$ designates the attachment to other groups in the compound of the formula I, wherein $X_1$-$X_{16}$ independently of one another is selected from N or C—R, with the proviso that in the groups of the formula 3 and 6, in each case one group from the groups $X_8/X_7$ and $X_{16}/X_{15}$ designates the attachment $\ell$ to the other groups in the compound of the formula I, wherein each R independently of any other is selected from a group composed of H, halogen, branched or linear, cyclic or open-chain $C_1$-$C_{20}$ alkyl, where hydrogen atoms of the $C_1$-$C_{20}$ alkyl may be substituted and C atoms of the $C_1$-$C_{20}$ alkyl may be replaced by heteroatoms; $C_2$-$C_{20}$ alkenyl, O-alkyl, S-alkyl, O-alkenyl, S-alkenyl, alkynyl, aryl, heteroaryl, wherein hydrogen atoms may be substituted in all groups; CN, NR'R'', with R' and R'' each independently of one another being selected from: H, branched or linear, cyclic or open-chain $C_1$-$C_{20}$ alkyl, where hydrogen atoms of the $C_1$-$C_{20}$ alkyl may be substituted and C atoms of the $C_1$-$C_{20}$ alkyl may be replaced by heteroatoms, wherein $R_1$ to $R_3$ each independently of one another are selected from a group composed of H, branched or linear, cyclic or open-chain $C_1$-$C_{20}$ alkyl, where hydrogen atoms of the $C_1$-$C_{20}$ alkyl may be substituted and C atoms of the $C_1$-$C_{20}$ alkyl may be replaced by heteroatoms; substituted or unsubstituted $C_2$-$C_{20}$ alkenyl, substituted or unsubstituted aryl, substituted or unsubstituted heteroaryl, CN, wherein each Q independently of any other is selected from S, O, Se, NR''', where R''' is defined as for $R_1$ to $R_3$, wherein the electron-withdrawing groups EWG1 and EWG2 independently of one another are selected from:

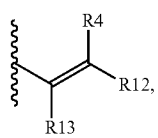

Formula 7

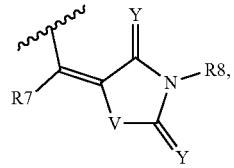

Formula 8

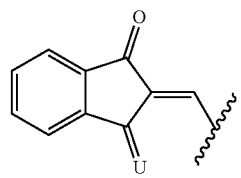

Formula 9 and $\ell$ designates the attachment to the groups T1 to T4 or the group Z in the compound of the formula I, wherein $R_4$ and $R_{12}$ each independently of one another is selected from H, CN, COOR, with the proviso that $R_4$ and $R_{12}$ cannot both be H, wherein R is selected from the same group of compounds as defined in the case of $R_1$ to $R_3$, wherein each $R_{13}$ independently of any other is selected from a group: H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, where, if the substituent $R_5$ or $R_6$ is present in the compound of the formula I, a ring closure between $R_5$ with $R_{13}$ or $R_6$ with $R_{13}$ is possible, with the proviso that the double bond from formula 11 is located in each case between $R_5$ and $R_{13}$ or between $R_6$ and $R_{13}$, wherein V is O, S; Y is O, S, $C(CN)_2$; and U is O, S, $C(CN)_2$, wherein $R_7$ and $R_8$ each independently of one another is selected from a group H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, where for each of the electron-withdrawing groups EWG1 and EWG2, each independently of one another in each case for each C═C double bond, both the E-isomer and the Z-isomer may be present, wherein the groups T1, T2, T3 and T4 each independently of one another are selected from:

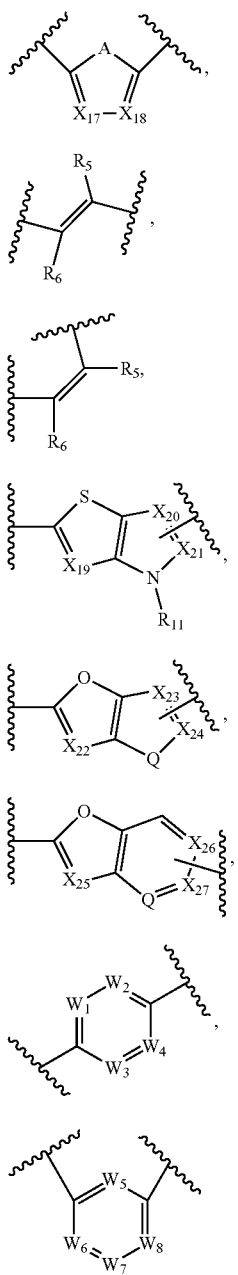

Formula 10

Formula 11

Formula 11*

Formula 12

Formula 13

Formula 14

Formula 15

Formula 16 wherein $i$ designates the attachment to the other groups in the compound of the formula I, wherein R5 and R6 each independently of one another is selected from a group: H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, wherein, if the substituent $R_{13}$ is present in the compound of the formula I, a ring closure may exist between $R_5$ with $R_{13}$ or $R_6$ with $R_{13}$, with the proviso that between $R_5$ and $R_{13}$ or between $R_6$ and $R_{13}$ in each case the double bond from formula 11 is located, is possible, wherein $W_1$ to $W_8$ each independently of one another is selected from N, CR, where R is defined as described above, wherein $X_{17}$ to $X_{27}$ independently of one another is selected from C—R, where R is defined as described above, and with the proviso that in the groups of the formulae 12, 13 and 14, in each case one group from the groups $X_{20}/X_{21}$, $X_{23}/X_{24}$ and $X_{26}/X_{27}$ designates the attachment $i$ to the other groups in the compound of the formula I, wherein A is S, O, NR"", Se, wherein Q is S, O, NR"", Se, and wherein for the groups A and Q, the substituent R"" in each case independently of any other is selected from H, CN, branched or linear, cyclic or open-chain $C_1$-$C_{20}$ alkyl, where the H atoms of the $C_1$-$C_{20}$ alkyl may be substituted; $C_2$-$C_{20}$ alkenyl, O-alkyl, S-alkyl, O-alkenyl, S-alkenyl, alkynyl, substituted or unsubstituted aryl, substituted or unsubstituted heteroaryl.

2. The compound according to claim 1, wherein the parameter c is 1.

3. The compound according to claim 1, wherein the electron-withdrawing groups EWG1 or EWG2 are the following group:

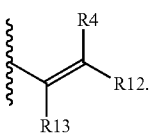

4. The compound according to claim 3, wherein $R_4$ and $R_{12}$ are CN.

5. The compound according to claim 1, wherein at least one of the parameters a, b, d and e is 0.

6. The compound according to claim 1, wherein c=1 and in the group Z, the group M is the group of formula 1:

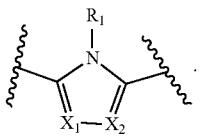

7. The compound according to claim 6, wherein $X_1$ and $X_2$ are C—R, with each R independently of any other selected from a group composed of H, halogen, branched or linear, cyclic or open-chain $C_1$-$C_{20}$ alkyl.

8. The compound according to claim 6, wherein in the group Z, the group N is the group of formula 4:

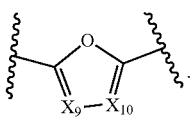

9. The compound according to claim 8, wherein $X_9$ and $X_{10}$ are C—R, with each R independently of any other being selected from a group composed of H, halogen, branched or linear, cyclic or open-chain $C_1$-$C_{20}$ alkyl.

10. The compound according to claim 5, wherein parameter b is 1 and group T2 is the group of formula 10:

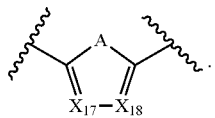

11. The compound according to claim 10, wherein A is S or O.

12. The compound according to claim 11, wherein in $X_{17}$ and $X_{18}$, R independently at each occurrence is selected from a group composed of H, halogen, branched or linear, cyclic or open-chain $C_1$-$C_{20}$ alkyl.

13. The compound according to claim 5, wherein parameter d=1 and the group T3 is selected from the groups of formulae 10 or 11:

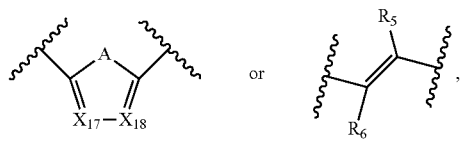

respectively.

14. The compound according to claim 13, wherein A ═S or O.

15. The compound according to claim 14, wherein R in $X_{17}$ and $X_{18}$ independently at each occurrence is selected from a group composed of H, halogen, branched or linear, cyclic or open-chain $C_1$-$C_{20}$ alkyl, $R_5$ and $R_6$ each independently of one another are selected from H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, and where, if the substituents $R_5$ and $R_6$ are present in the compound, a ring closure may exist between $R_5$ with $R_{13}$ or $R_6$ with $R_{13}$, with the proviso that the double bond from formula 11 is located between $R_5$ and $R_{13}$ or between $R_6$ and $R_{13}$.

16. The compound according to claim 15, where the ring closure between the substituents $R_5$ with $R_{13}$ or $R_6$ with $R_{13}$ is present in the form of an optionally substituted cyclopentenyl ring or of an optionally substituted cyclohexenyl ring.

17. The compound according to claim 5, wherein the parameter e=1 and the group T4 is a group of formula 10 or 11:

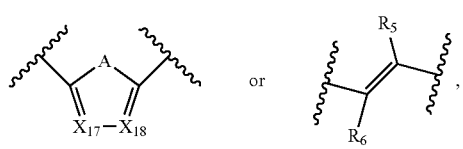

respectively.

18. The compound according to claim 17, wherein A ═O or S.

19. The compound according to claim 18, wherein in $X_{17}$ and $X_{18}$, R is selected independently of any other from a group composed of H, halogen, branched or linear, cyclic or open-chain $C_1$-$C_{20}$ alkyl.

20. The compound according to claim 5, wherein the parameter a=1 and the group T1 is a group of formula 10 or 11:

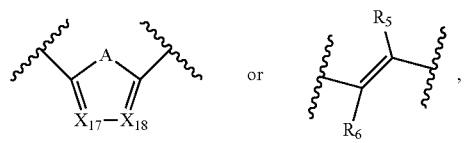

respectively.

21. The compound according to claim 20, wherein A ═S or O.

22. The compound according to claim 21, wherein R in $X_{17}$ and $X_{18}$ independently at each occurrence is selected from a group composed of H, halogen, branched or linear, cyclic or open-chain $C_1$-$C_{20}$ alkyl, and R5 and R6 are each selected independently of one another from H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, where, if the substituent $R_5$ and $R_6$ is present in the compound, a ring closure between $R_5$ with $R_{13}$ and also between $R_6$ with $R_{13}$ is may exist, with the proviso that the double bond from formula 11 is located between $R_5$ and $R_{13}$ or between $R_6$ and $R_{13}$.

23. The compound according to claim 21, having the following structural formula II:

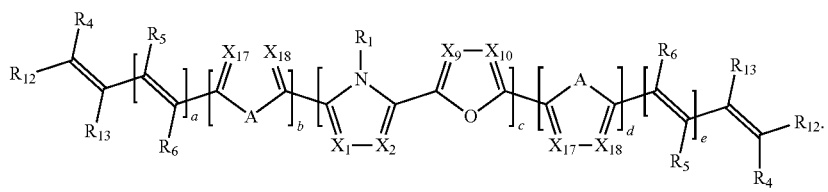

24. The compound according to claim 23, wherein each A is O or S independently of one another.

25. The compound according to claim 23, wherein independently of one another $X_{17}$, $X_{18}$, $X_1$, $X_2$, $X_9$ and $X_{10}$ are C—R, where R independently at each occurrence is selected from a group composed of H, halogen, branched or linear, cyclic or open-chain $C_1$-$C_{20}$ alkyl, and $R_6$ and $R_6$ each independently of one another are selected from H, CN, F, aryl, heteroaryl, $C_2$-$C_{20}$ alkenyl, alkynyl, branched or linear, cyclic or open-chain $C_1$-$C_{20}$ alkyl, where hydrogen atoms of the $C_1$-$C_{20}$ alkyl may be substituted, and where, if the substituents $R_5$ and $R_6$ are present, a ring closure may be formed between $R_5$ with $R_{13}$ or $R_6$ with $R_{13}$.

26. The compound according to claim 23, wherein the parameter c is 1.

27. The compound according to claim 23, wherein the parameter b is 1.

28. The compound according to claim 23, wherein the parameter e is 1.

29. The compound according to claim 23, wherein $R_4$ and $R_{12}$ each independently of one another are selected from H and CN, with the proviso that $R_4$ and $R_{12}$ cannot both be H.

30. Use of the compound according to claim 1 in an organic electronic component.

31. The use according to claim 30, wherein the organic electronic component is an organic photoactive element, optionally a solar cell.

32. An organic electronic device comprising the compound according to claim 1.

33. The organic electronic device according to claim 32, comprising an electrode and a counterelectrode and at least one organic photoactive layer between the electrode and the counterelectrode, wherein the organic photoactive layer comprises the compound.

* * * * *